US012702842B2

(12) United States Patent
Cassar et al.

(10) Patent No.: US 12,702,842 B2
(45) Date of Patent: Aug. 11, 2026

(54) SYSTEMS AND METHODS FOR EVALUATING NEUROMODULATION BASED ON EVOKED POTENTIALS

(71) Applicant: Duke University, Durham, NC (US)

(72) Inventors: Isaac Cassar, Durham, NC (US); Warren Grill, Durham, NC (US)

(73) Assignee: Duke University, Durham, NC (US)

( * ) Notice: Subject to any disclaimer, the term of this patent is extended or adjusted under 35 U.S.C. 154(b) by 577 days.

(21) Appl. No.: 17/500,459

(22) Filed: Oct. 13, 2021

(65) Prior Publication Data

US 2022/0111213 A1 Apr. 14, 2022

Related U.S. Application Data

(60) Provisional application No. 63/091,520, filed on Oct. 14, 2020.

(51) Int. Cl.
*A61N 1/36* (2006.01)

(52) U.S. Cl.
CPC ..... *A61N 1/36189* (2013.01); *A61N 1/36062* (2017.08); *A61N 1/36082* (2013.01); *A61N 1/36132* (2013.01); *A61N 1/36146* (2013.01)

(58) Field of Classification Search
CPC ................................................. A61N 1/36082
See application file for complete search history.

(56) References Cited

U.S. PATENT DOCUMENTS

2014/0243931 A1* 8/2014 Parker ................ A61N 1/36071 607/62
2014/0378941 A1* 12/2014 Su ........................ A61B 5/4255 604/506
2018/0221644 A1* 8/2018 Grill .................. A61N 1/36067
2022/0096842 A1* 3/2022 Jackson ............. A61N 1/36153

FOREIGN PATENT DOCUMENTS

AU 2018204710 A1 * 7/2018 ......... A61N 1/36178

OTHER PUBLICATIONS

Devergnas A, Wichmann T. Cortical potentials evoked by deep brain stimulation in the subthalamic area. Front Syst Neurosci. May 13, 2011;5:30. doi: 10.3389/fnsys.2011.00030. PMID: 21625611; PMCID: PMC3097379. (Year: 2011).*

Dustman et al. The Downstate Series of Research in Psychiatry and Psychology, vol. 2. Springer, Boston, MA. https://doi.org/10.1007/978-1-4684-3462-0_14 (Year: 1979).*

(Continued)

*Primary Examiner* — Benjamin J Klein
*Assistant Examiner* — Willow Grace Welch
(74) *Attorney, Agent, or Firm* — Casimir Jones, S.C.; Peter J. Schlueter

(57) ABSTRACT

The present disclosure provides systems and methods relating to neuromodulation. In particular, the present disclosure provides systems and methods for evaluating the efficacy of neuromodulation therapy using evoked potential (EPs). The systems and methods disclosed herein facilitate the evaluation of both parameter-dependent and system-dependent changes in EPs as indicators of therapeutic efficacy.

23 Claims, 19 Drawing Sheets
(18 of 19 Drawing Sheet(s) Filed in Color)

(56) References Cited

OTHER PUBLICATIONS

Little et al. Adaptive deep brain stimulation in advanced Parkinson disease. Ann Neurol. Sep. 2013;74(3):449-57. doi: 10.1002/ana.23951. Epub Jul. 12, 2013. PMID: 23852650; PMCID: PMC3886292. (Year: 2013).*

Boulogne et al. Cortico-cortical and motor evoked potentials to single and paired-pulse stimuli: An exploratory transcranial magnetic and intracranial electric brain stimulation study. Hum Brain Mapp. Nov. 2016;37(11):3767-3778. doi: 10.1002/hbm.23274. PMID: 27312488; PMCID: PMC6867359. (Year: 2016).*

Miocinovic et al. Cortical Potentials Evoked by Subthalamic Stimulation Demonstrate a Short Latency Hyperdirect Pathway in Humans. J Neurosci. Oct. 24, 2018;38(43):9129-9141. doi: 10.1523/JNEUROSCI.1327-18.2018. Epub Sep. 10, 2018. PMID: 302017PMCID: PMC6199405. (Year: 2018).*

Benabid et al., Deep brain stimulation of the subthalamic nucleus for the treatment of Parkinson's disease. Lancet Neurol. Jan. 2009;8(1):67-81.

Kumaravelu et al., Model-based deconstruction of cortical evoked potentials generated by subthalamic nucleus deep brain stimulation. J Neurophysiol. Aug. 1, 2018;120(2):662-680.

Little et al., Adaptive deep brain stimulation in advanced Parkinson disease. Ann Neurol. Sep. 2013;74(3):449-57.

Miocinovic et al., Cortical Potentials Evoked by Subthalamic Stimulation Demonstrate a Short Latency Hyperdirect Pathway in Humans . . . The Journal of Neuroscience. 2018; 38 (43): 1327-18.

Onslow et al., Quantifying phase-amplitude coupling in neuronal network oscillations. Prog Biophys Mol Biol. Mar. 2011;105(1-2):49-57.

Tinkhauser et al., Beta burst dynamics in Parkinson's disease Off and On dopaminergic medication. Brain. Nov. 1, 2017;140(11):2968-2981.

Volkmann et al., Introduction to the programming of deep brain stimulators. Mov Disord. 2002;17 Suppl 3:S181-7.

* cited by examiner

FIG. 2C
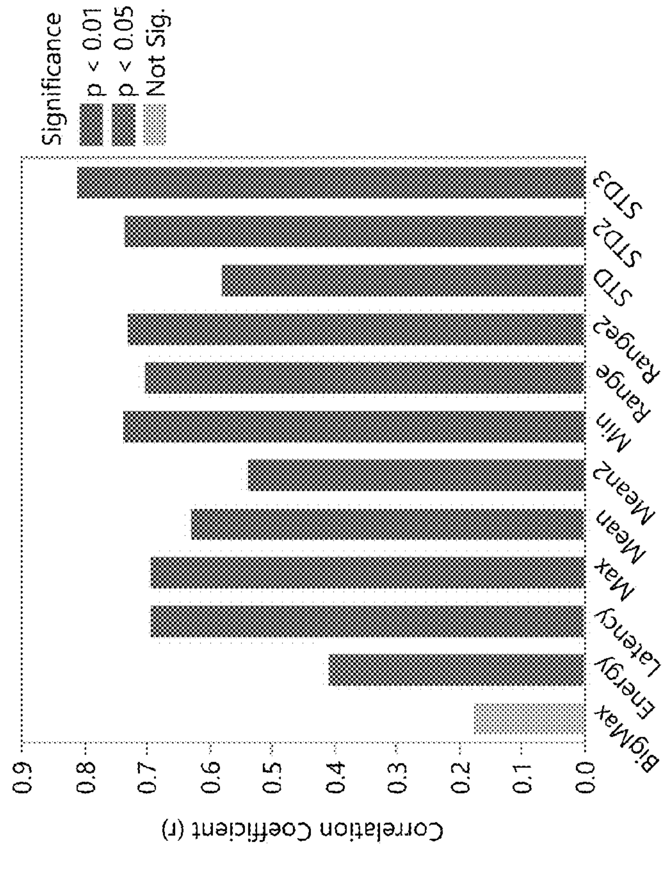
FIG. 2D
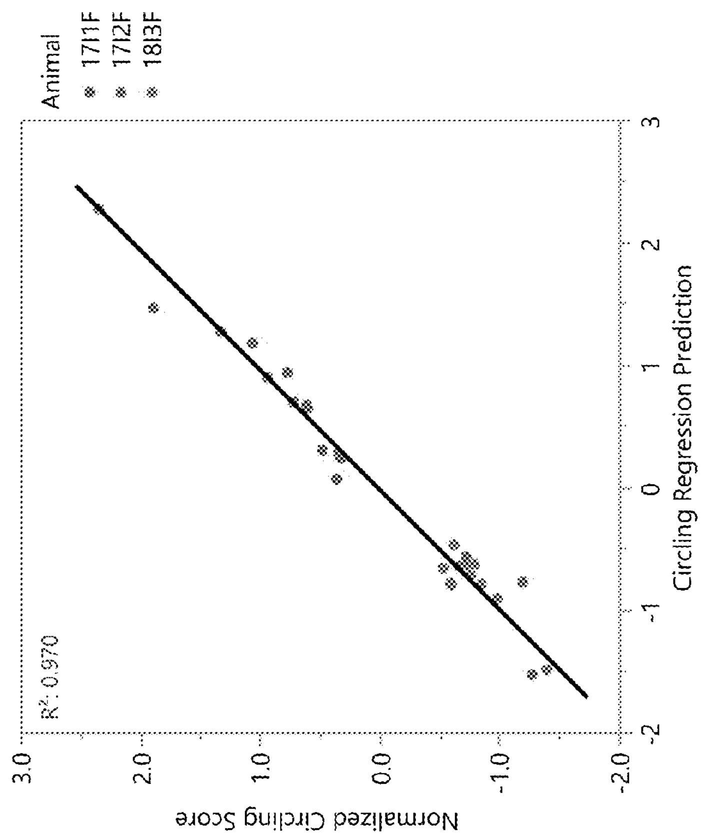
FIGS. 2A-2D (cont'd)

FIG. 5A
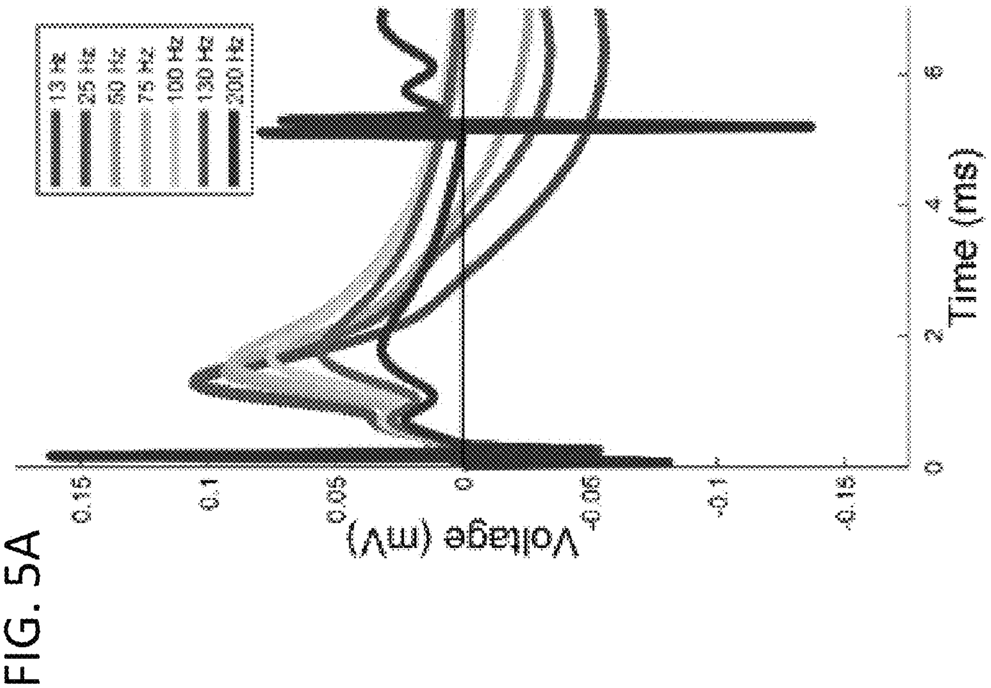
FIG. 5B
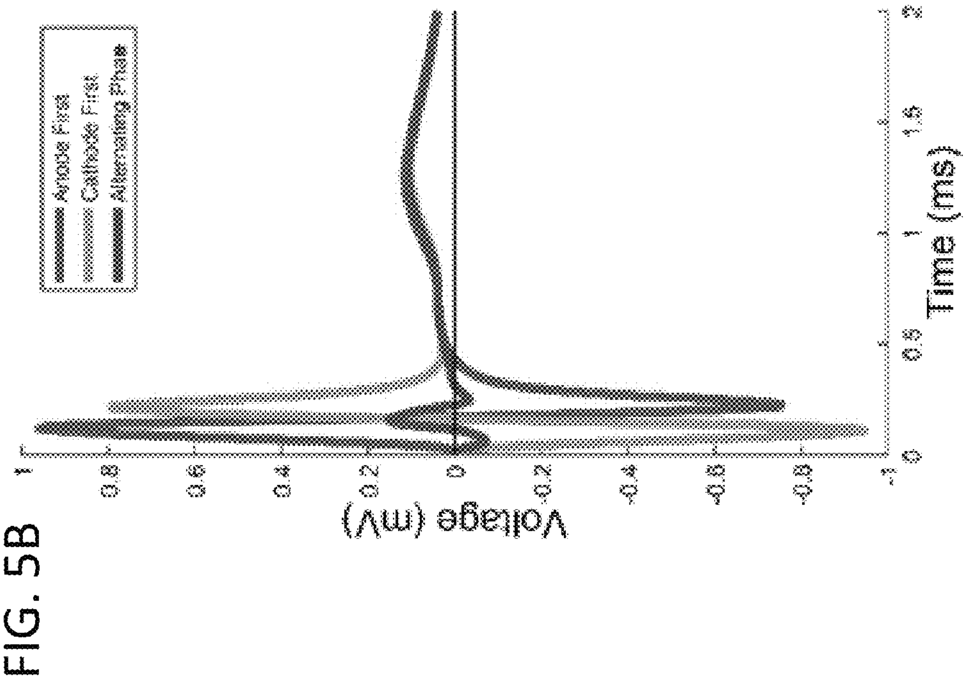
FIGS. 5A-5C

FIG. 7A
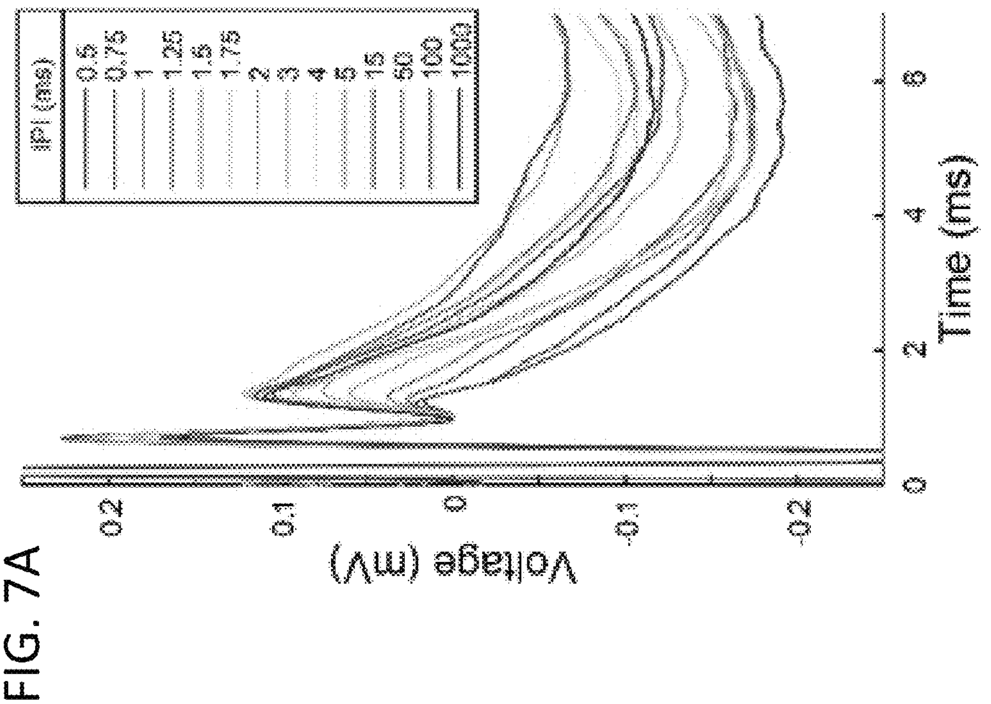
FIG. 7B
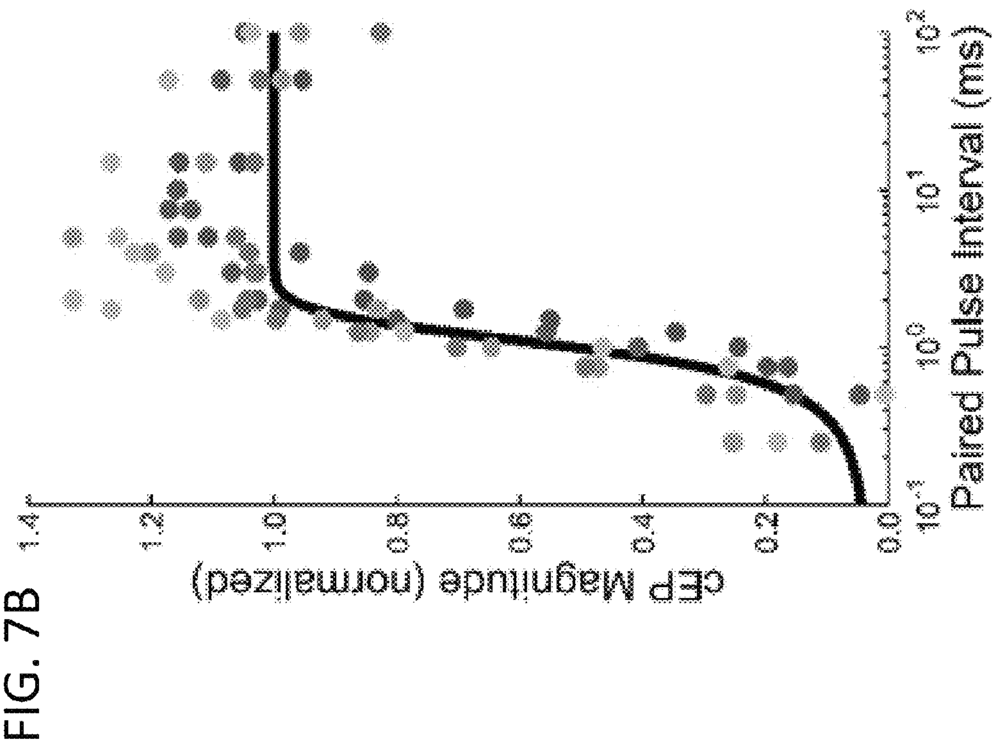
FIGS. 7A-7B

FIG. 8A
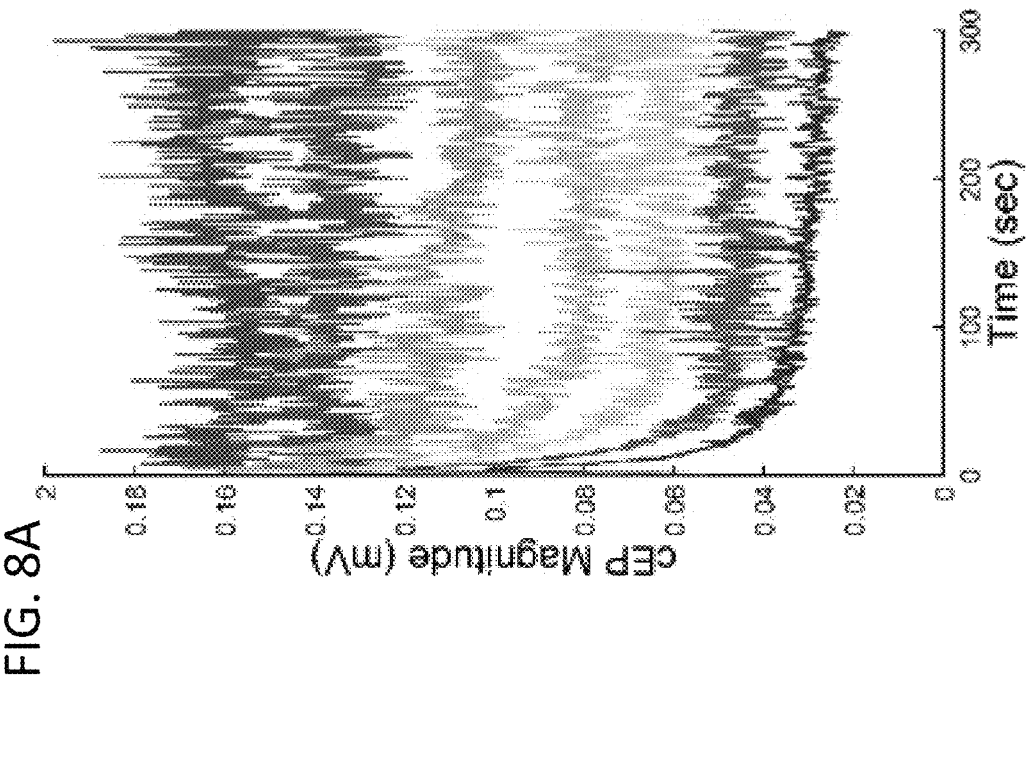
FIG. 8B
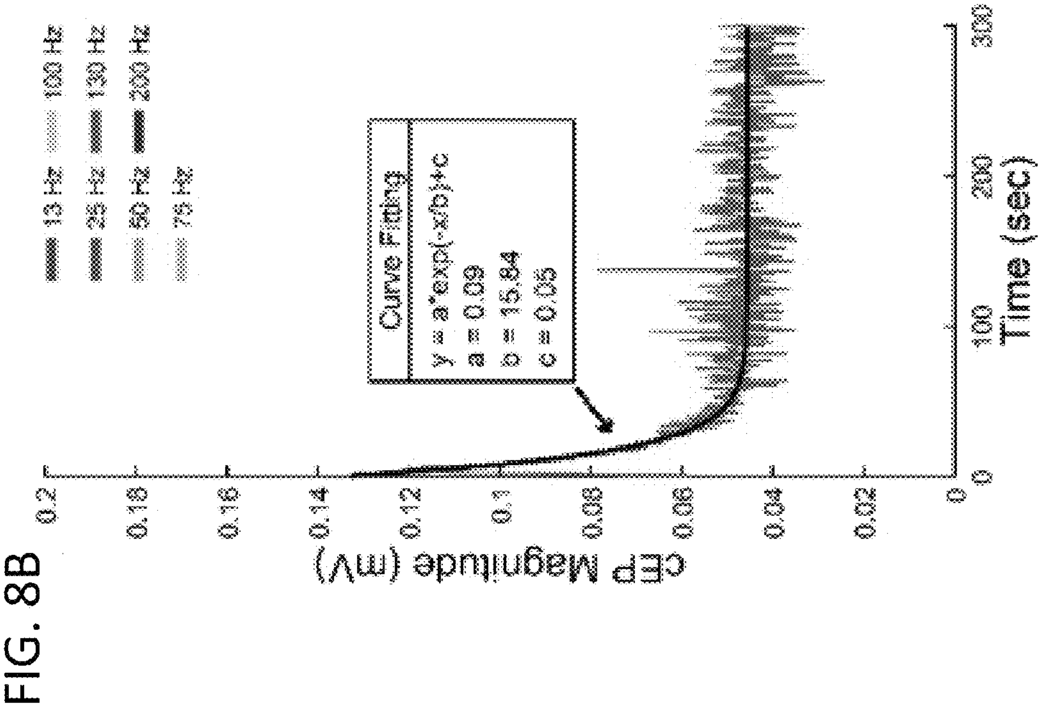
FIGS. 8A-8B
cEP Magnitude (mV)
Time (sec)
13 Hz
100 Hz
25 Hz
130 Hz
50 Hz
200 Hz
75 Hz
Curve Fitting
y = a*exp(-x/b)+c
a = 0.09
b = 15.84
c = 0.05
cEP Magnitude (mV)
Time (sec)

FIG. 14B
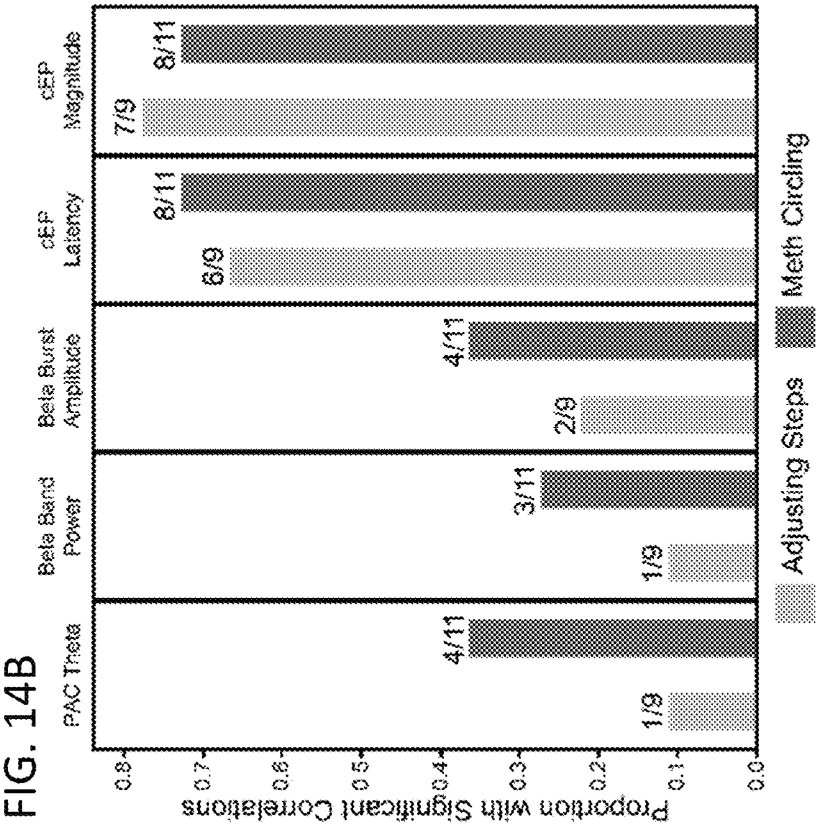
FIG. 14A
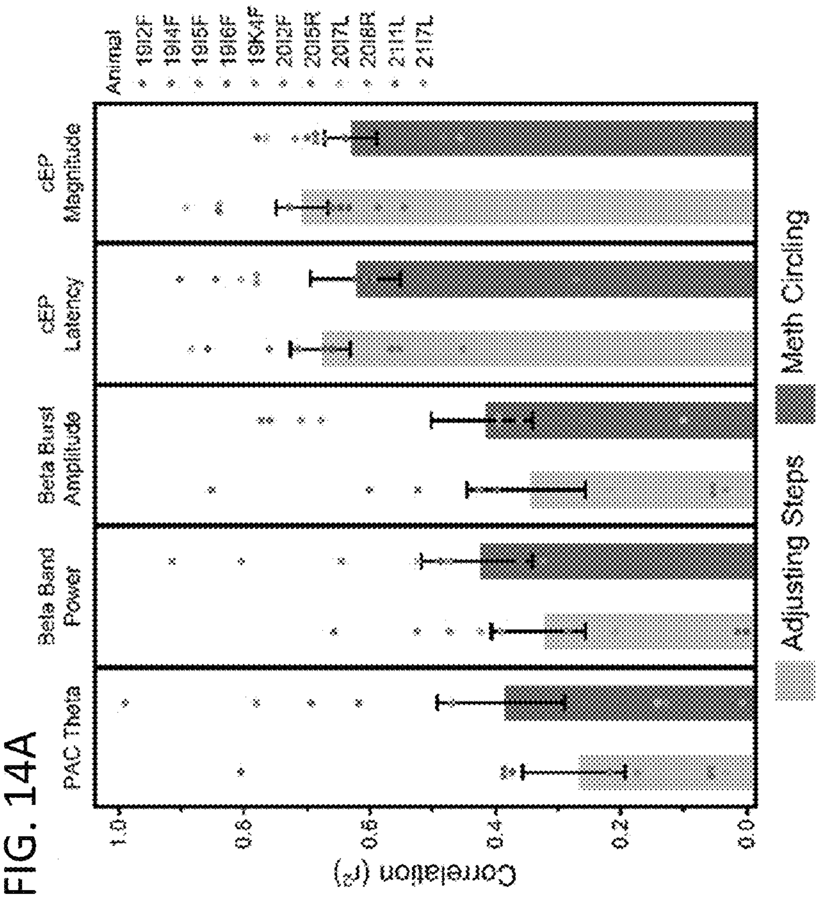
FIGS. 14A-14B

SYSTEMS AND METHODS FOR EVALUATING NEUROMODULATION BASED ON EVOKED POTENTIALS

RELATED APPLICATIONS

This application claims priority to and the benefit of U.S. Provisional Patent Application No. 63/091,520 filed Oct. 14, 2020, which is incorporated herein by reference in its entirety for all purposes.

STATEMENT REGARDING FEDERALLY SPONSORED RESEARCH OR DEVELOPMENT

This invention was made with government support under NS040894 awarded by the National Institute of Health. The government has certain rights in the invention.

FIELD

This present disclosure provides systems and methods relating to neuromodulation. In particular, the present disclosure provides systems and methods for evaluating the efficacy of neuromodulation therapy using evoked potentials (EPs). The systems and methods disclosed herein facilitate the evaluation of both parameter-dependent and system-dependent changes in EPs as indicators of therapeutic efficacy.

BACKGROUND

Neuromodulation therapies, including deep brain stimulation (DBS), spinal cord stimulation (SCS), sacral nerve stimulation (SNS), and vagus nerve stimulation (VNS), treat a wide variety of clinical conditions. One of the primary challenges in implementing neuromodulation therapies is determining the proper "dose" of the therapy. Dose for neural stimulation devices is determined by the electrical stimulation settings or stimulation parameters that are delivered. These parameters include the electrode contacts that are active, the stimulation amplitude and polarity (anodic, +, or cathodic, −) delivered to each contact, the stimulation pulse repetition frequency, the stimulation pulse duration, the shape of the stimulation pulse, and the temporal pattern of stimulation (timing between the stimulation pulses), where the pattern can include duty cycle, bursts, random, or other non-random patterns of varying intervals between stimulation pulses. Additionally, the appropriate parameter settings (those that produce the desired clinical effect without producing an unwanted side effect) may vary over time due to movement of the electrode (e.g., lead migration), changes in the surrounding tissue impedance (e.g., foreign body response or scarring), disease progression, the medication status of the patient, changes in the state of the patient (e.g., walking versus sitting or awake versus sleeping), and/or changes in the response to stimulation, including tachyphylaxis.

One method for assessing the effects of stimulation parameter settings is by electrically recording the aggregate neural activated evoked following stimulation, commonly referred to as the evoked potential (EP), evoked compound action potential (ECAP), or DBS local evoked potential (DLEP). The EP is dependent on the stimulation parameters used, and the shape, magnitude, latency, and number of peaks of the EP indicate the relative quantity and types of neurons activated by stimulation. Additionally, the EP may change following repetitive stimulation, and the degree and manner of this change may be used to determine the effects of stimulation of neuronal activity, on changes in symptom, and/or on side effects. For example, the EP following DBS may decline in magnitude over time due to higher incidences of axonal conduction failure, and this may contribute to the therapeutic mechanism of DBS. Therefore, the changes in the shape and characteristics of the EP provide a proxy for changes in symptoms produced by application of stimulation relief.

SUMMARY

Embodiments of the present disclosure include a method of determining efficacy of a neuromodulation therapy based on evoked potential (EP). In accordance with these embodiments, the method includes (i) obtaining a reference EP recording from a subject, (ii) obtaining a variable EP recording from the subject, and (iii) identifying at least one feature that is different between the reference EP recording and the variable EP recording.

In some embodiments, at least one stimulation parameter has been altered with respect to the reference EP recording. In some embodiments, the at least one different feature of the variable EP recording obtained by altering the at least one stimulation parameter correlates with a disease indication, a change in symptom, and/or a change in side effect. In some embodiments, the at least one different feature of the variable EP recording obtained by altering the at least one stimulation parameter correlates with charge, energy, and/or power required for stimulation.

In some embodiments, the variable EP recording is obtained from at least a second timepoint with respect to the reference EP recording. In some embodiments, the variable EP recording is obtained at the at least second timepoint using stimulation parameters that are substantially identical with respect to the reference EP recording. In some embodiments, the at least one different feature of the variable EP recording correlates with a disease indication, a change in symptom, and/or a change in side effect. In some embodiments, the at least one different feature of the variable EP recording correlates with charge, energy, and/or power required for stimulation.

In some embodiments, the at least one different feature of the variable EP recording is indicative of a system-dependent change. In some embodiments, system-dependent changes include, but are not limited to, alterations in network state, ion accumulation, movement of the electrode (e.g., lead migration), synaptic plasticity, neural excitability, changes in the surrounding tissue impedance (e.g., foreign body response or scarring), disease progression, the medication status of the patient, changes in the state of the patient (e.g., walking versus sitting or awake versus sleeping), changes in the response to stimulation, including tachyphylaxis, and any combinations thereof.

In some embodiments, the at least one stimulation parameter comprises: (i) number and/or location of active electrode contacts; (ii) stimulation amplitude and polarity delivered to each contact; (iii) stimulation pulse repetition frequency; (iv) stimulation pulse duration; (v) stimulation pulse shape; and (vi) temporal pattern of stimulation. In some embodiments, the temporal pattern of stimulation comprises duty cycle, bursts, random patterns, and non-random patterns.

In some embodiments, the at least one feature of the reference or variable EP recording comprises: (i) maximum peak voltage; (ii) peak latency; (iii) voltage differences from a maximum voltage; (iv) minimum trough value; (v) mean waveform value; (vi) voltage standard deviation; (vii) sum of voltage squared; (viii) voltage difference from the voltage at a set time point; and (ix) signal power present in specific spectral bands of the EP and any combinations thereof.

In some embodiments, the reference EP recording and the variable EP recording are obtained in response to pulses within a stimulation train. In some embodiments, the reference EP recording and the variable EP recording are obtained from a single pulse. In some embodiments, the reference EP recording and the variable EP recording are obtained by averaging individual responses to multiple repetitions of pulses within a stimulation train. In some embodiments, the reference EP recording and the variable EP recording are obtained by summing individual responses to multiple repetitions of pulses within a stimulation train over a set time period. In some embodiments, the reference EP recording and the variable EP recording are obtained as part of a closed-loop stimulation protocol.

In some embodiments, methods of determining efficacy of a neuromodulation therapy based on EP further include repeating steps (ii) and (iii) to generate a variable EP signature that comprises a plurality of different features with respect to the reference EP. In some embodiments, the variable EP signature correlates with a disease indication, a change in symptom, and/or a change in side effect. In some embodiments, the variable EP signature correlates with charge, energy, and/or power required for stimulation.

In some embodiments, the method further comprises altering at least one stimulation parameter to treat a symptom and/or reduce a side effect in the subject. In some embodiments, the treatment is provided to the subject as part of deep brain stimulation (DBS), spinal cord stimulation (SCS), sacral nerve stimulation (SNS), vagus nerve stimulation (VNS), peripheral nerve stimulation (PNS), or cranial nerve stimulation.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

FIG. 5A includes the average cEP during five-minute recordings at seven different stimulation frequencies (13, 25, 50, 75, 100, 130, 200 Hz) from a representative animal using alternating-phase stimulation. Note the reduced magnitude and increased latency of the cEP with increasing stimulation frequency. Representative example of alternating-phase stimulation at 13 Hz are shown in FIG. 5B. In red is the averaged anode-first stimulation, in green is the averaged cathode-first stimulation, and in blue is the average cEP from alternating-phase stimulation. Note that the stimulation artifact from 0-0.5 ms is largely eliminated, but the cEP from 1-2 ms remains. Representative raw ECoG trace during 13 Hz stimulation showing the relative magnitude of the cEP are shown in FIG. 5C. In red is the stimulation artifact, and in blue is the first five ms following each stimulation pulse that contains the short-latency cEP.

FIG. 6B includes cEP magnitude and latency as a function of stimulation frequency and pulse width (PW; 60, 90, 120 μs) (n=5). Data in the Single Condition group is normalized to the 120 μs PW value. For the Single Condition group, there were significant effects of frequency, PW, and freq*PW on the cEP magnitude, but only a significant effect of frequency on the cEP latency. However, for the Each Condition group there was only a significant effect of frequency on both the cEP magnitude and latency. FIG. 6C includes cEP magnitude and latency as a function of stimulation frequency during an awake vs. sevoflurane anesthetized state (n=6). Data in the Single Condition group is normalized to the Awake value. For the Single Condition group, there were significant effects of frequency, sevoflurane, and freq*sevo on the cEP magnitude, and significant effects of frequency and sevoflurane on the cEP latency. However, for the Each Condition group there was only a significant effect of frequency on the cEP magnitude, but significant effects of both frequency and sevo on the cEP latency.

FIGS. 7A-7B: cEP magnitude as a function of paired pulse interval, which varied from 0.5-100 ms (n=5). FIG. 7A includes the average cEP waveform across paired pulse intervals in a representative animal. Note that the waveform from approximately time 0-1.0 ms is the stimulation artifact.

FIG. 7B includes each cEP magnitude normalized to its value using 1 Hz stimulation. Colors represent individual values from each rat. The data were fit with a sigmoid with its maximum value capped at 1 to determine the relative refractory period, which was t50=0.985 ms. Notably, there was also a hyperexcitable region from approximately 5-10 ms.

FIGS. 8A-8B: Change in cEP magnitude over time. The cEP magnitude over five minute trials at seven different stimulation frequencies (13, 25, 50, 75, 100, 130, 200 Hz) from a representative animal is shown in FIG. 8A. The cEP is averaged over 500 ms windows. Note that there is only an observable change over time for stimulation frequencies ≥50 Hz. FIG. 8B includes an example of the exponential fitting process using the 130 Hz trial in FIG. 8A.

FIG. 9A includes the cEP magnitude binned at six different time points (5, 10, 30, 60, 120, 300 sec) at seven different stimulation frequencies (13, 25, 50, 75, 100, 130, 200 Hz), normalized to each animal's peak cEP magnitude (n=7). Each curve was fit to both a linear and exponential model, and the AICc Weight revealed that an exponential fit was superior for stimulation frequencies ≥50 Hz (Table 3). For these higher frequencies, the cEP magnitude for each animal at each stimulation frequency were then fit to three-parameter exponential decay curves (n=7). FIG. 9B includes the exponential decay time constant; FIG. 9C includes the steady state value; and FIG. 9D includes the y-intercept. A repeated measures linear regression of each term revealed a significant effect of stimulation frequency for the steady state value and the y-intercept, but not for the time constant (Table 4).

FIG. 13A includes the behavioral scores for both tasks. Note that a higher score in the adjusting steps task and a lower score in the methamphetamine-induced circling task indicate superior reduction in motor symptoms. FIG. 13B includes the PAC modulation index in the theta/low amplitude range (phase 1-8 Hz, amplitude 10-50 Hz). FIG. 13C includes the beta band power (13-30 Hz), normalized to the broadband power (4-90 Hz). FIG. 13D includes the average low beta band (13-20 Hz) burst amplitude. FIG. 13E includes the cEP latency. FIG. 13F includes the cEP magnitude.

FIGS. 14A-14B: Correlation of biomarkers with symptom reduction for the adjusting steps task (n=9) and methamphetamine-induced circling (n=11). PAC—Theta is the phase-amplitude coupling modulation index in the theta/low amplitude range (phase 1-8 Hz, amplitude 10-50 Hz), the Beta Band Power is the power in the beta range (13-30 Hz) normalized to the broadband power (4-90 Hz), and the Beta Burst Amplitude is the average amplitude of the low beta band (13-20 Hz) bursts. FIG. 14A includes the Pearson's product-moment correlation coefficient squared for each animal; error bars indicate the SEM. FIG. 14B includes the proportion of animals with significant correlation probabilities less than 0.05. Across behavioral tasks, both cEP biomarkers, and especially the cEP magnitude, consistently demonstrated the strongest correlations, largely due to the low variability between animals.

FIG. 15A illustrates the probe-pulse technique, which enables consistent probing of the cEP while changing the stimulation frequency/amplitude. The probe-pulses, delivered at 13 Hz in this case, are kept at the same amplitude while the other pulses are allowed to vary. During the offline cEP quantification only the cEPs from the probe-pulses are included in the analysis. FIG. 15B includes representative results from the methamphetamine-induced circling task using the probe-pulse technique with stimulation frequencies of (13, 75, 130, 200 Hz) and amplitudes of (60%, 80%, 100%), each titrated to the individual rat's therapeutically effective amplitude (n=4). In the top panel is the behavioral score, with lower scores indicating superior reduction in motor symptoms. In the middle panel is the cEP magnitude and in the bottom panel is the cEP latency, with each normalized to their values at 13 Hz. FIG. 15C illustrates the correlation of the cEP magnitude and latency with circling score for each animal. All correlations had a statistically significant Pearson's product-moment correlation coefficient, with average $r^2$ values for the cEP magnitude and latency of 0.650 and 0.754, respectively.

DETAILED DESCRIPTION

Figure 1:
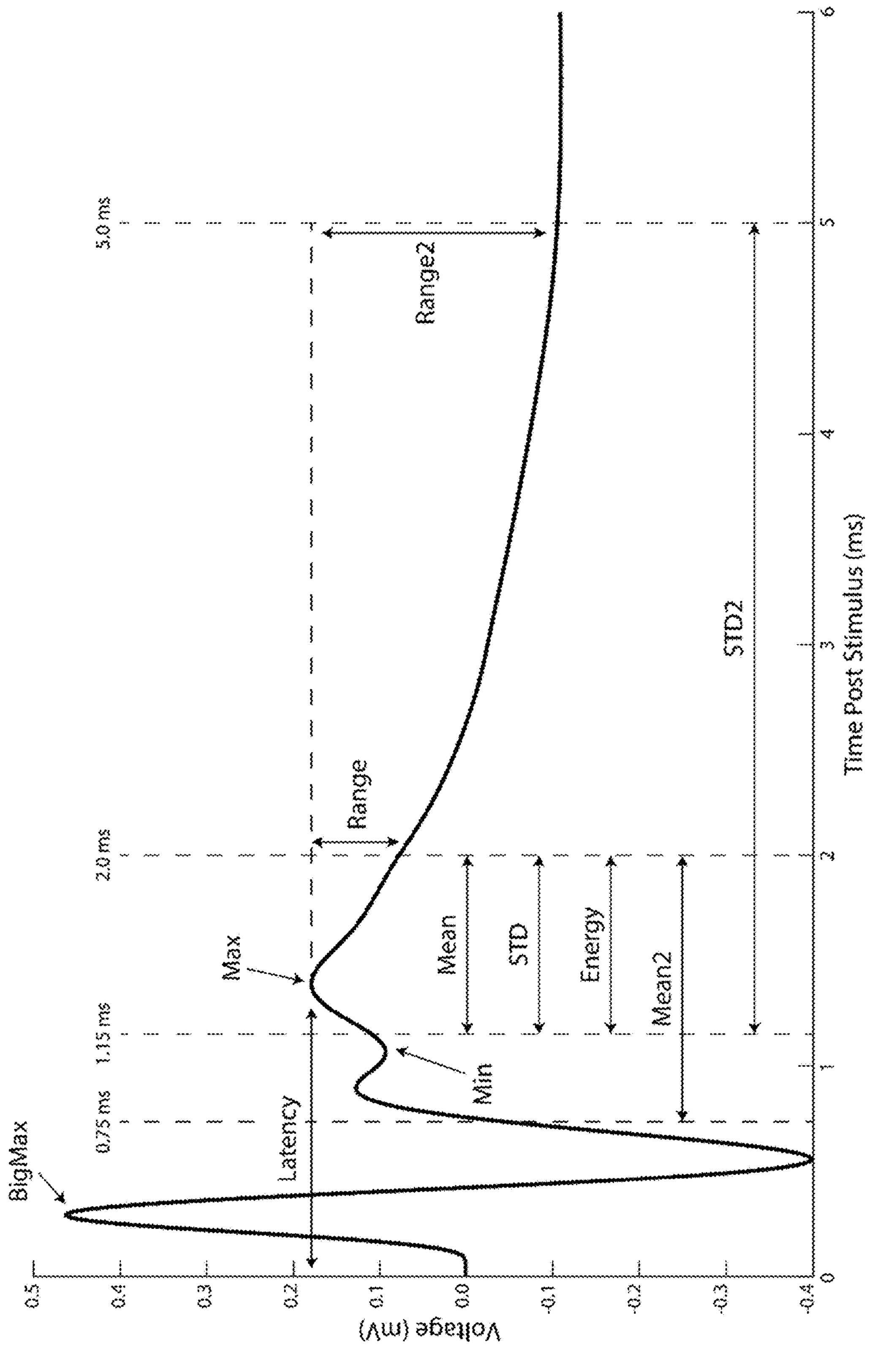
FIG. 1: Representative data illustrating the average evoked potential recorded from the cortex (cortical evoked potential, cEP) from 10 Hz deep brain stimulation of the subthalamic nucleus in a rat. Labels identify potential features that can be extracted from the EP. (See Table 1 for descriptions of each feature.)

Embodiments of the present disclosure provide systems and methods relating to neuromodulation. In particular, the present disclosure provides systems and methods for evaluating the efficacy of neuromodulation therapy using evoked potential (EPs). The systems and methods disclosed herein facilitate the evaluation of both parameter-dependent and system-dependent changes as indicators of therapeutic efficacy.

As described further herein, monitoring the EP during stimulation can provide a means for temporally assessing relative changes between the shape of the EP and various other characteristics at different time points. For example, there are generally two distinct means by which an EP can change. Firstly, the EP may change as a result of a change(s) to (or adjustments in) one or more stimulation parameter settings (e.g., contact selection, stimulation pulse amplitude, stimulation pulse duration, stimulation pulse repetition rate, stimulation pulse pattern and the like), and these changes in the EP can be considered parameter-dependent changes. Secondly, the EP may change as a result of a physiological change(s) (e.g., degree of symptom, medication status, activity level, network state, ion accumulation, lead migration, synaptic plasticity, and the like). As described further herein, when stimulation parameters are generally fixed, the changes observed in the EP can be considered system-dependent changes. Parameter-dependent changes may be useful indicators of therapeutic efficacy, such as when selecting stimulation contacts that elicit the strongest activation of a desired neuron population. The system-dependent changes are also useful in that they can be indicators of the relative change in total fiber activation over time relative to a certain amount of initial activation, or indicating whether a stimulation lead has moved and is activating a different group of neurons. However, in clinical settings, it is often times challenging (if not impossible) to distinguish between parameter-dependent changes in the EP from system-dependent changes in the EP. Therefore, embodiments of the present disclosure provide methods and systems related to the use of probe pulses to isolate parameter-dependent changes and system-dependent changes in the EP.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (e.g., a monkey, such as a cynomolgus or rhesus monkey, chimpanzee, etc.) and a human) In some embodiments, the subject may be a human or a non-human. In one embodiment, the subject is a human. The subject or patient may be undergoing various forms of treatment.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a treatment to a subject that is not at the time of administration afflicted with the disease. "Preventing" also refers to preventing the recurrence of a disease or of one or more symptoms associated with such disease.

"Therapy" and/or "therapy regimen" generally refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

"Evoked potential" or "EP" as used herein generally refers to the electrical potential in a specific pattern recorded from a specific part of the nervous system of a subject. EPs measure the electrophysiologic responses of the nervous system of a subject to various stimuli. EPs can be used as a means for assessing the effects of stimulation parameter settings by electrically recording the aggregate neural activated evoked following stimulation. EPs are also referred to as evoked compound action potential (ECAP), or DBS local evoked potential (DLEP). For the purposes of the present disclosure, the term "evoked potential" refers to any of these types of recordings. As described further herein, various characteristics of an EP can be used as a means for selecting or adjusting one or more stimulation parameter settings.

"Parameter-dependent change(s)" as used herein generally refer to changes in an EP as a result of altering one or more electrical stimulation parameter settings, including but not limited to, electrode contact selection, stimulation pulse amplitude, stimulation pulse duration, stimulation pulse repetition rate, and the like. As described further herein, the methods of the present disclosure can distinguish a parameter-dependent change from a system-dependent change.

"System-dependent change(s)" as used herein generally refer to changes in an EP as a result of a physiological change in a subject. For example, system-dependent changes can include, but are not limited to, alterations in network state, ion accumulation, movement of the electrode (e.g., lead migration), synaptic plasticity, neural excitability, changes in the surrounding tissue impedance (e.g., foreign body response or scarring), disease progression, the medication status of the subject, changes in the state of the subject (e.g., walking versus sitting or awake versus sleeping), changes in the response to stimulation, including tachyphylaxis, and any combinations thereof. As described further herein, the methods of the present disclosure can distinguish a system-dependent change from a parameter-dependent change.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, neurobiology, microbiology, genetics, electrical stimulation, neural stimulation, neural modulation, and neural prosthesis described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. EVOKED POTENTIALS

EPs for Use in Stimulation Parameter Selection and Adjustment. Embodiments of the present disclosure include the use of EP (e.g., shape and various features, as shown in FIG. 1) as a means to evaluate, select, and/or adjust stimulation parameters when delivering neuromodulation therapy to a subject. As shown in FIG. 1, there are many different features and characteristics of EPs that can serve as indicators of therapeutic efficacy and/or system functionality. Potential features include, but are not limited to, the latency of a peak or trough, the magnitude of a peak or trough, the area under the curve during a specified interval, the range of potentials during a specified interval, the energy of the waveform during a specified interval, the standard deviation during a specified interval, and signal power present in specific spectral bands of the EP, among others. Exemplary definitions of the characteristics of an EP are shown in FIG. 1, and exemplary calculations of these characteristics are shown in Table 1 (below).

TABLE 1

Exemplary calculations of cEP characteristics.

| Feature | Calculation |
|---|---|
| BigMax (mV) | Maximum voltage of stimulus artifact during time 0.0-1.0 ms |
| Max (mV) | Maximum voltage of peak during time 1.15-2.0 ms |
| Latency (ms) | Latency in ms of the peak during time 1.15-2.0 ms |
| Range (mV) | Difference between Max and voltage at 2.0 ms |
| Range2 (mV) | Difference between Max and voltage at 5.0 ms |
| Min (mV) | Minimum value of trough during time 0.9-1.5 ms |
| Mean (mV) | Mean value of waveform during time 1.15-2.0 ms |
| Mean2 (mV) | Mean value of waveform during time 0.75-2.0 ms |
| STD (mV) | Standard deviation of the voltage during time 1.15-2.0 ms |
| STD2 (mV) | Standard deviation of the voltage during time 1.15-5.0 ms |
| STD3 (mV) | STD + standard deviation of the voltage during time 3.0-5.0 ms |
| Energy (mV^2) | Sum of the voltage squared during time 1.15-2.0 ms |

Figures 2A, 2B, 2C, 2D:
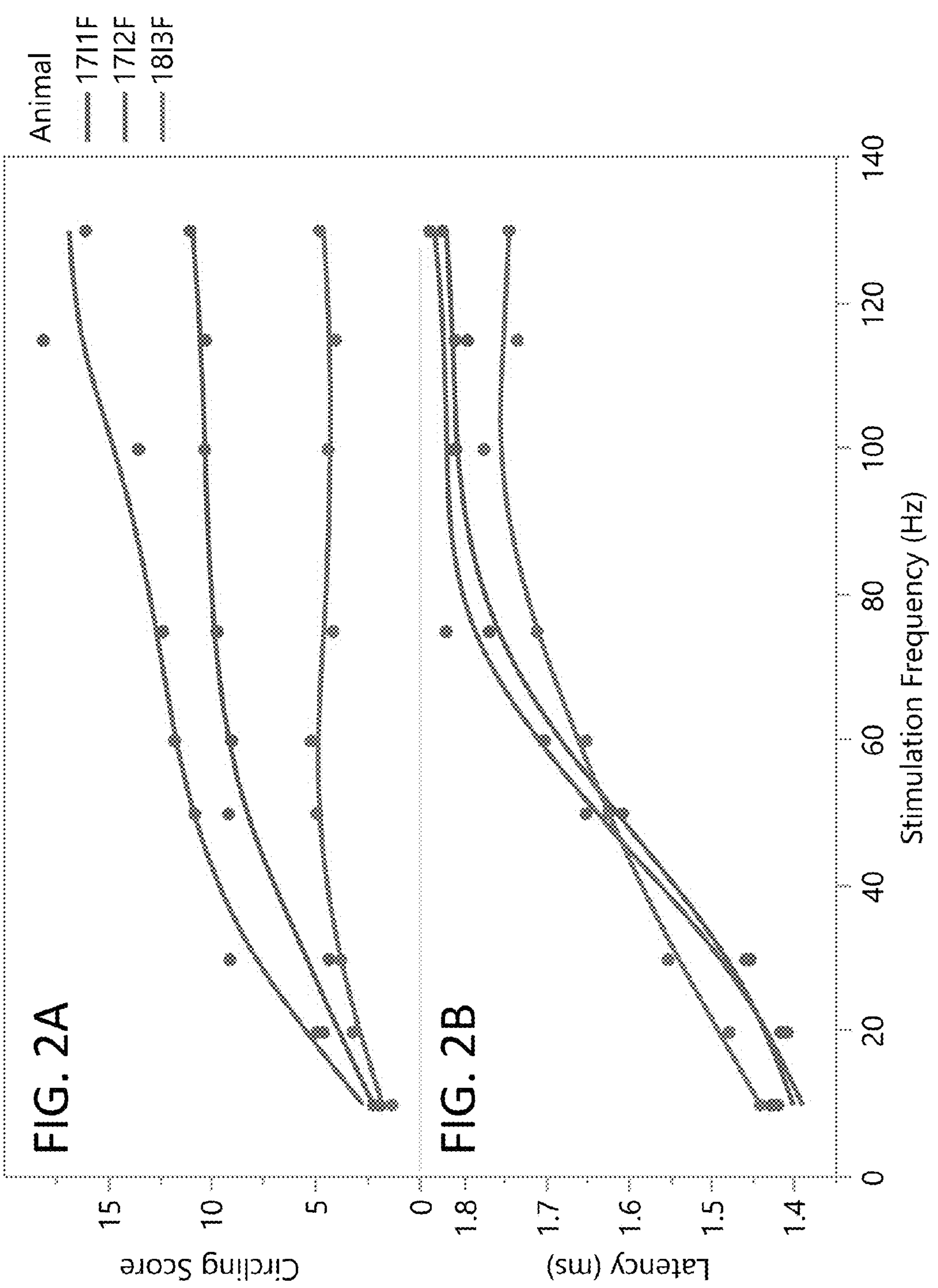
FIGS. 2A-2D: cEP features correlate with DBS motor improvement. Methamphetamine induced circling score shows improvement in circling as a function of stimulation frequency in three rats (FIG. 2A). Latency of cEP peak as a function of stimulation frequency in the same rats as FIG. 2A (FIG. 2B). The absolute value of the correlation coefficients for each feature from Table 1 with the circling scores in FIG. 2A (FIG. 2C). Lasso regression with corrected Akaike Information Criterion (AICc) Validation using each feature from Table 1 to predict the Circling Scores in FIG. 2A (FIG. 2D). Each feature and the circling scores were first normalized using the Z-Score. The resulting prediction had an $R^2$ of 0.970.

As described further herein, embodiments of the present disclosure include examples of the utility of using the shape and/or characteristics of the EP as a means to evaluate, select, and/or adjust one or more stimulation parameter settings (e.g., comparing a variable EP recording to a reference EP recording). In one embodiment, features in the cortical evoked potential (cEP) following deep brain stimulation (DBS) of the subthalamic nucleus (STN) correlated significantly with the efficacy of DBS in relieving the symptoms of parkinsonism in rats (modeled with neurotoxin 6-hydroxydopamine (6-OHDA) administration). STN DBS was applied at varying frequencies from about 10 Hz to about 130 Hz in 6-OHDA lesioned rats, and motor performance was assessed via methamphetamine-induced circling. Each rat exhibited the typical response to DBS with different pulse repetition frequencies, and motor symptoms improved with increased stimulation pulse repetition frequency, before leveling off at approximately 100 Hz (FIG. 2A). Several features of the cEP showed dependence on the pulse repetition frequency that paralleled the changes in parkinsonian symptoms, including, for example, the latency of the peak, as shown in FIG. 2B. Other selected features that showed a statistically significant correlation with motor symptoms are shown in FIG. 2C, with multiple correlation coefficients greater than r=0.7. These data demonstrate that one or more features of an EP can be used to assess one or more aspects of neuromodulation therapy (e.g., by comparing a reference EP to a variable EP).

In another embodiment of the present disclosure, multiple features of the EP can be combined to create a composite metric or EP signature that is representative of, or a diagnostic proxy for, the effects of electrical stimulation in a subject. In some embodiments, the effects include, but are not limited to, changes in neuronal activity, changes in one or more symptoms, alleviation of one or more side effects, as well as effects on stimulation system parameters, including but not limited to, the charge, energy, or power required for stimulation. For example, in some embodiments, a generalized linear model (GLM) can be used to combine the features of the EP to obtain a more accurate prediction of the symptom response. A GLM (Lasso regression with corrected Akaike Information Criterion (AICc) Validation) was used on all of the normalized features and a predictor of normalized motor symptom was obtained with an $R^2$ of 0.97 (FIG. 2D). Thus, embodiments of the present disclosure include the use of both individual features of the EP as well as a combination of features (e.g., an EP signature) as an indicator to evaluate, select, and/or adjust one or more parameters of stimulation to achieve, for example, relief of a symptom, to reduce, minimize or eliminate a side effect, and/or to reduce the total charge, power, or energy required for effective stimulation.

In some embodiments, the shape or characteristics of the EP can be used either during initial stimulation parameter selection and/or as a part of feedback control during stimulation (e.g., ongoing closed-loop stimulation). For example, during initial parameter tuning, changes in the EP can be monitored for each stimulation setting, and the stimulation parameter settings that elicit the most desirable characteristic(s) (e.g., target characteristic) of the EP can be selected. This tuning can either be done empirically by a technician, or through the use of an automated algorithm. In another embodiment, the shape or characteristics of the EP can be used as part of a feedback signal during, for example, closed-loop stimulation. Both processes can be repeated as many times as necessary to enhance neuromodulation therapy. However, if the stimulation parameters are changed during the course of therapy, such as with closed-loop stimulation in which the stimulation amplitude is titrated, it can be challenging to determine whether observed EP changes are due to parameter-dependent changes in the EP from system-dependent changes in the EP. Depending on system parameters and the desired outcome of the neuromodulation therapy, alternative means for using EP as a feedback control signal may become important. In accordance with this, embodiments of the present disclosure also include the use of probe pulses to isolate parameter-dependent changes and system-dependent changes in the EP, and thereby enable the use of the EP as a robust control signal for feedback control.

Probe Pulses to Distinguish Parameter-Dependent Changes and System-Dependent Changes. As provided herein, when stimulation parameters are generally fixed, the changes observed in the EP can be considered system-dependent changes. Parameter-dependent changes may be useful indicators of therapeutic efficacy, such as when selecting stimulation contacts that elicit the strongest activation of a desired neuron population. The system-dependent changes are also useful in that they can be indicators of the relative change in total fiber activation over time relative to a certain amount of initial activation, or indicating whether a stimulation lead has moved and is activating a different group of neurons. However, in clinical settings, it is often times challenging (if not impossible) to distinguish between parameter-dependent changes in the EP from system-dependent changes in the EP. Therefore, embodiments of the present disclosure provide methods and systems related to the use of probe pulses to isolate parameter-dependent changes and system-dependent changes in the EP.

Figure 3:
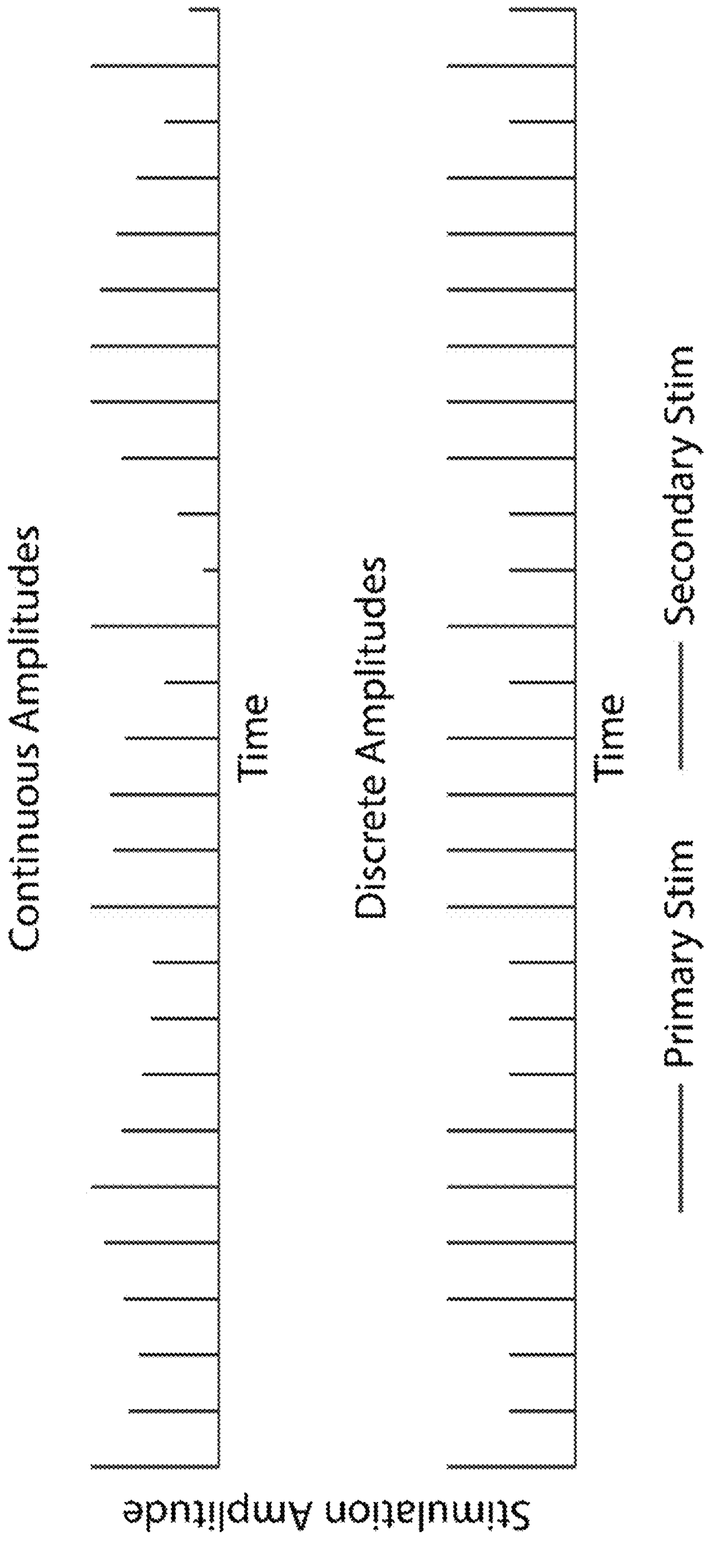
FIG. 3: Representative diagram illustrating methods for varying the stimulation amplitude using a second probe stimulation train to evoke repeatedly a reference EP superposed with the first functional stimulation train.

In accordance with these embodiments, the methods of the present disclosure also include application of two superimposed stimulation trains to determine whether a given change in a feature of an EP is a parameter-dependent change or a system-dependent change. In some embodiments, a first functional stimulation train that may have its stimulation parameters regulated according to whatever control system is in use, and a second probe stimulation train at a lower frequency with fixed stimulation parameters (FIG. 3) can be delivered. By comparing the EPs generated by the first and second stimulation trains, parameter-dependent changes and system-dependent changes in the EP can be distinguished. The isolation of parameter-dependent changes and system-dependent changes in the EP thereby enables the use of the EP as a feedback control signal.

For example, the second probe stimulation train is used to evoke an EP with fixed stimulation parameters (e.g., reference EP) and the probe EP can be compared with the desired EP or the EP measured at another point in time (e.g., variable EP). In this manner, it is possible to ascertain system-dependent changes, which can then be used by the control system to adjust the stimulation parameters used in the first functional stimulation train. The second probe stimulation pulse repetition frequency can be set at a subharmonic of the first functional stimulation pulse repetition frequency so that the secondary probe pulses simply replace those of the first functional stimulation train on a periodic basis. The first functional stimulation parameters can be adjusted continuously between determined high and low parameter values or set to one of a discrete number of predetermined settings depending on the characteristics of the probe EP.

In another embodiment of the present disclosure, the secondary probe stimulation train can be used to account for dynamic changes in the EP that result, for example, from relative movement of the electrode with respect to the neurons that generate the evoked potential. In the case of epidural spinal cord stimulation, for example, the EP can be used to adjust the stimulation parameters to produce a targeted level of activation of the nerve fibers in the dorsal columns of the spinal cord. The shape and characteristics of the EP from dorsal column nerve fiber stimulation depend on the stimulation parameter settings (parameter-dependent EP), as these parameters determine the number and pattern of dorsal column nerve fiber stimulation. However, the shape and characteristics of the EP from dorsal column nerve fiber stimulation also depend on the position of the epidural recoding electrode array with respect to the dorsal column nerve fibers (system-dependent EP), and this relationship changes, for example, with the posture of the individual. The use of a secondary probe stimulation train can be used to measure the dynamic changes in the EP that occur as a result of changes in the relative position of the electrode and the stimulation parameters can be adjusted accordingly. Further, the use of probe pulses can be used to isolate parameter-dependent changes and system-dependent changes in the EP evoked by spinal cord stimulation.

Using the EP to Update the Stimulation Pulse Repetition Frequency. In some embodiments, the EP can be used as a feedback control signal during closed-loop stimulation in which at least one stimulation parameter is adjusted. For example, the stimulation pulse repetition frequency can be adjusted, while the values of the other stimulation parameters (e.g., contact, amplitude, stimulation pulse duration) remain fixed. One embodiment of this method can include adjusting the stimulation pulse repetition frequency between predetermined discrete values (e.g., low, medium, high). The stimulation pulse repetition frequency can be switched to one of these values dependent on one or more features of the EP. In another embodiment, the method includes continuously varying the stimulation pulse repetition frequency between a predetermined low and high value, for example. The stimulation pulse repetition frequency can then be continuously adjusted within that range, dependent on one or more features of the EP.

Figures 4A, 4B:
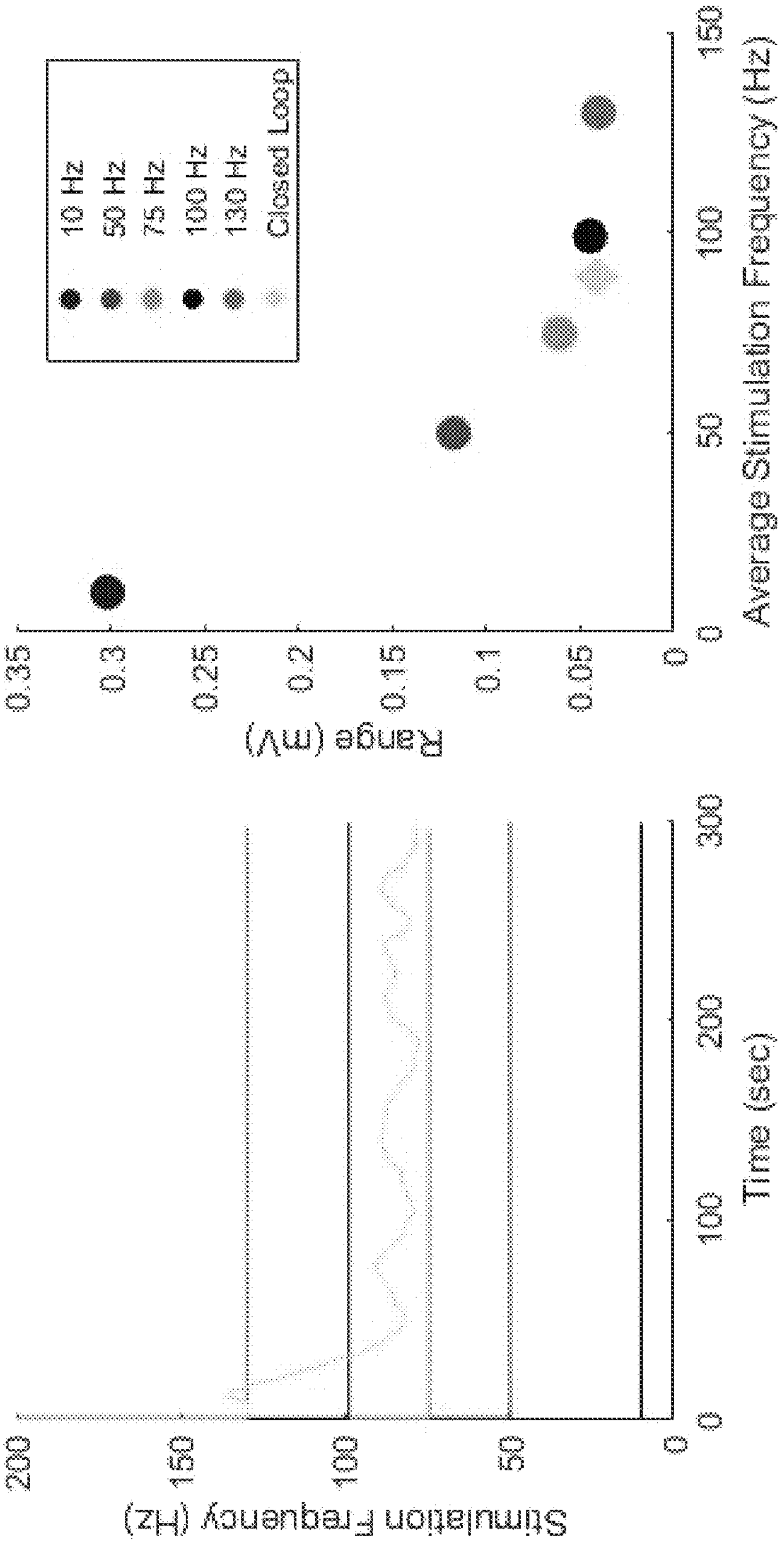
FIGS. 4A-4B: Application of closed loop stimulation based on the EP in a rat. Five different constant stimulation frequencies were used in five-minute trials, and then a sixth closed loop stimulation trial was performed for five minutes. Applied stimulation frequencies for each of the trials (FIG. 4A). Average values for the EP 'Range' for each of the stimulation methods (FIG. 4B). The closed loop stimulation was designed to maintain the same Range value as the 100 and 130 Hz stimulation trials, while minimizing average stimulation frequency.

As an example, feedback control of the stimulation pulse repetition frequency, based upon the range of the EP signal, was implemented in an animal model. The evoked potential recorded from the cortex (cEP) following STN DBS was used as a control signal for closed-loop stimulation in rat. A series of five minute sessions with constant stimulation pulse repetition frequency was first applied, with stimulation pulse repetition frequency set to rates from about 10 Hz to about 130 Hz. The EP feature "Range" was used as the control signal because it showed a clear dependence on stimulation pulse repetition frequency that leveled off at approximately 100 Hz (FIG. 4). A simple proportional controller was used, with the stimulation pulse repetition frequency adjusted by the relative difference between the recorded EP Range and a preset desired EP Range (0.04 mV in this example) that was obtained based on the values of the reference EP measured during stimulation with a constant stimulation pulse repetition frequency. A stimulation pulse repetition frequency reduction term was also included, which reduced the stimulation pulse repetition frequency to lower values at a rate proportional to the difference between the current stimulation pulse repetition frequency and 50 Hz. This minimized the stimulation pulse repetition frequency, which reduced the electrical energy required for stimulation as well as the likelihood that stimulation will generate an unwanted side effect. Additionally, limits to the stimulation pulse repetition frequency were set between about 10 and about 200 Hz. The stimulation was set to begin at about 130 Hz, with updates every 0.2 sec. Closed-loop stimulation maintained the desired EP value while minimizing the stimulation frequency. The performance of the closed-loop controller was superior to 100 Hz stimulation, and the controller produced a lower average EP value and a lower average stimulation frequency.

As is recognized by one of ordinary skill in the art, standard clinical stimulation parameter tuning is an ad hoc and empirical process in which the efficacy of each parameter set is based on observed symptom reduction, which can take minutes to hours to manifest. This process is inefficient, requires a highly trained clinician, involves repeat tuning sessions, and is unlikely to yield the optimal parameter settings. However, as disclosed further herein, the EP may be a useful quantitative biomarker to aid in stimulation parameter selection, as it is easy to record, quantifiable in real time, and appears to be highly consistent across subjects. The EP may assist with selecting the stimulation contact, amplitude, pulse width, and frequency, among other stimulation parameters.

Additionally, with the growing use of directional, multi-contact electrode leads, it is no longer as feasible to use a trial-and-error approach to determine which contact or contacts should be used for stimulation. For example, it has been demonstrated clinically that stimulation contacts that induce higher EP magnitudes during low frequency stimulation correspond with those selected as the most therapeutically effective. The results of the present disclosure support this observation and indicate that higher rates of cortical activation, which would occur with higher EP magnitudes at a given frequency, generate stronger informational lesions, thus are more effective at desynchronizing pathological oscillations, and thus would be more effective at treating symptoms.

However, symptom reduction is not the only factor involved in the selection of stimulation parameters; it is equally important to avoid motor and/or sensory side effects, which can be caused by incorrect electrode contact location, for example. As described further herein, the EP may also be used to quantify these motor and/or sensory side effects, as side effects from STN DBS are often due to the unintended activation of fibers in the internal capsule, and capsular activation can be recorded by the EP. Algorithms can be thus designed that quickly and efficiently test all possible contact pairs and select the contact(s) that induce the highest EP magnitude that is beyond a certain latency, for example. An accurate EP measurement can be quantified in less than a second of stimulation; thus, the whole process of contact selection could take a matter of minutes, dramatically speeding up stimulation parameter tuning. The cEP can also be recorded while anesthetized, so this contact selection process could be done intraoperatively to ensure accurate lead location as well.

Furthermore, the EP may also be used to help determine the optimal stimulation amplitude and/or pulse width. Embodiments of the present disclosure indicate that higher EP magnitudes are beneficial, for example, and that higher stimulation amplitudes and longer pulse widths increase the EP magnitude. However, high amplitudes and pulse widths can also cause side effects. Similar to the contact selection, an algorithm can thus be designed to sweep through each possible stimulation amplitude and/or pulse width and find the setting(s) that induce the highest cEP magnitude that is beyond a desired latency. Additionally, to reduce the number of parameters tested, evidence indicates that shorter pulse widths increase the therapeutic window between symptom reduction and side effects, so the pulse width could be kept fixed at a low duration and only the stimulation amplitude adjusted by the algorithm.

3. METHODS OF TREATMENT AND DIAGNOSIS

In accordance with the embodiments described above, the present disclosure provides methods of determining efficacy of a neuromodulation therapy based on the shape and characteristics of an EP (see, e.g., FIG. 1). In some embodiments, the method includes (i) obtaining a reference EP recording from a subject, (ii) obtaining a variable EP recording from the subject, and (iii) identifying at least one feature that is different between the reference EP recording and the variable EP recording.

In some embodiments, a reference EP recording is obtained by delivering electrical stimulation (e.g., neuromodulation therapy) to a subject according to a given set of stimulation parameters. This reference EP recording can serve as a baseline or control against which a variable EP recording can be compared and at least one different feature of the reference EP and the variable EP can be identified. In some embodiments, at least one stimulation parameter can be altered with respect to the reference EP recording, such that at least one different feature of the reference EP and the variable EP can be identified. In some embodiments, identifying at least one different feature of the variable EP recording obtained by altering the at least one stimulation parameter correlates with, for example, a disease indication, a change in symptom, and/or a change in side effect. That is, altering a stimulation parameter and comparing the reference EP to the variable EP can lead to the identification of a feature that has changed, and this altered feature can be indicative of a therapeutically relevant outcome associated with the electrical stimulation delivered to a subject. In some embodiments, at least one different feature of the variable EP recording obtained by altering at least one stimulation parameter correlates with one or more aspects of the neuromodulation system, including but not limited to, charge, energy, and/or power required for stimulation. In general, changes in EP as a result of altering one or more stimulation parameters are referred to as parameter-dependent changes. In accordance with these embodiments, stimulation parameters that can be altered as part of the methods of the present disclosure include, but are not limited to: (i) number and/or location of active electrode contacts; (ii) stimulation amplitude and polarity delivered to each contact; (iii) stimulation pulse repetition frequency; (iv) stimulation pulse duration; (v) stimulation pulse shape; and (vi) temporal pattern of stimulation. In some embodiments, the temporal pattern of stimulation comprises duty cycle, bursts, random patterns, and non-random patterns.

Embodiments of the present disclosure also include obtaining a variable EP recording from at least a second timepoint with respect to the reference EP recording. In some embodiments, the variable EP recording is obtained at a second timepoint using stimulation parameters that are substantially identical with respect to the reference EP recording. That is, by obtaining a variable EP at a different time point while the stimulation parameters are held substantially constant allows for the comparison of the reference EP (e.g., at time point 1) to the variable EP (e.g., at timepoint 2) in order to identify a feature that has changed, and this altered feature can be indicative of a therapeutically relevant outcome associated with the electrical stimulation delivered to a subject. In some embodiments, at least one different feature of the variable EP obtained at a second timepoint with respect to the reference EP correlates with one or more aspects of the neuromodulation system, including but not limited to, charge, energy, and/or power required for stimulation. In general, changes in EP that occur by altering the time of stimulation delivery are referred to as system-dependent changes. In some embodiments, system-dependent changes include, but are not limited to, alterations in network state, ion accumulation, movement of the electrode (e.g., lead migration), synaptic plasticity, neural excitability, changes in the surrounding tissue impedance (e.g., foreign body response or scarring), disease progression, the medication status of the patient, changes in the state of the patient (e.g., walking versus sitting or awake versus sleeping), changes in the response to stimulation, including tachyphylaxis, and any combinations thereof.

Thus, the embodiments of the present disclosure include methods of using EP or EP signatures as a diagnostic proxy for evaluating neuromodulation therapy, and also methods of differentiating parameter-dependent changes in EP from system-dependent changes in EP, which leads to more accurate assessments of symptoms and side effects and more effective therapy.

In accordance with these embodiments, features of the reference EP recording and the variable EP recording can include, but are not limited to: (i) maximum peak voltage; (ii) peak latency; (iii) voltage differences from a maximum voltage; (iv) minimum trough value; (v) mean waveform value; (vi) voltage standard deviation; (vii) sum of voltage squared; (viii) voltage difference from the voltage at a set time point; and (ix) signal power present in specific spectral bands of the EP and any combinations thereof (see, e.g., FIG. 1 and Table 1).

In some embodiments, the reference EP recording and the variable EP recording are obtained from a single pulse. In other embodiments, the reference EP recording and the variable EP recording are obtained in response to pulses within a stimulation train. In some embodiments, the reference EP recording and the variable EP recording are obtained by averaging individual responses to multiple repetitions of pules within a stimulation train. In some embodiments, the reference EP recording and the variable EP recording are obtained as part of a closed-loop stimulation protocol. Additionally, because it is possible that stimulation over time may have cumulative effects with respect to a given therapeutic outcome (e.g., symptom reduction), embodiments of the present disclosure also include methods for assessing an EP on a "per-second" basis. For example, in some embodiments, the total cumulative activation during stimulation can be quantified as the sum of individual responses to multiple pulses over a set time period (e.g., activation per-second).

In some embodiments, the methods of the present disclosure further include repeating the steps of obtaining a variable EP from a subject and identifying at least one feature that is different between the reference EP and the variable EP such that a variable EP signature is generated. The variable EP signature can comprise a plurality of different features with respect to the reference EP. In some embodiments, the variable EP signature correlates with a disease indication, a change in symptom, and/or a change in side effect. In other embodiments, the variable EP signature correlates with charge, energy, and/or power required for stimulation.

In some embodiments, the methods of the present disclosure further include altering at least one stimulation parameter to treat a symptom and/or reduce a side effect in the subject. The methods of the present disclosure can be performed as part of any neuromodulation treatment protocol, including but not limited to, deep brain stimulation (DBS), spinal cord stimulation (SCS), sacral nerve stimulation (SNS), vagus nerve stimulation (VNS), peripheral nerve stimulation (PNS), or cranial nerve stimulation.

4. MATERIAL AND METHODS

To assess the effects of STN DBS on hypokinetic motor symptoms, the unilateral 6-OHDA lesioned rat was used, which is a validated model of Parkinson's disease that shows responses similar to human PD patients during regular and nonregular temporal patterns of stimulation. Thirty female Sprague Dawley rats (250-300 g) were implanted unilaterally with stimulating microelectrodes in the STN and a bone screw above M1 for electrocorticography (ECoG). The rats were rendered hemi-parkinsonian via unilateral infusion of 6-OHDA into the medial forebrain bundle (MFB). In one set of experiments, the ECoG was recorded during an awake, freely-moving state while stimulation was applied. The ECoG was used to quantify the change in cEP features to different conditions and parameters of stimulation. In the second set of experiments, the ECoG was recorded during electrical stimulation at seven different stimulation frequencies (13, 25, 50, 75, 100, 130, 200 Hz) while the rats performed behavioral tasks to assess hypokinetic symptoms. This ECoG signal was then used to calculate the correlation between different electrophysiological biomarkers and symptom reduction across different stimulation frequencies.

2.1 Electrode Implantation and 6-OHDA Lesioning. All animal care and experimental procedures were approved by the Duke University Institutional Animal Care and Use Committee (Durham, NC). When not performing experiments, animals were housed under USDA- and AAALAC-compliant conditions, with free access to food and water with a 12 h/12 h light/dark cycle. Rats were single-housed post-implantation but given extra environmental enrichment. Stereotactic surgery was conducted under 3.0-3.5% sevoflurane anesthesia using aseptic technique and coordinates from a rat brain atlas. Heart rate, oxygen saturation, and body temperature were monitored throughout the surgery, and the body temperature was maintained between ~35-37° C. with a heated water blanket. For analgesia, meloxicam (2 mg/kg SC) and bupivacaine (<2 mg/kg) were administered ~15 min prior to incision. To prevent infection, enrofloxacin (Baytril, 5-10 mg/kg SC) was administered both prior to incision and 24 h after, and antibiotic ointment was applied to the incision site post-implantation. The cannula and electrodes were implanted unilaterally and ipsilateral to each other, with the hemisphere randomized between the rats. Implantations were performed using a stereotaxic electrode manipulator and inserted manually at a rate of approximately 100 μm/sec. One stimulating microelectrode array (2×2, platinum-iridium, 75 μm diameter, 0.3 mm inter-electrode spacing, and 10 kΩ impedance; Microprobes, Gaithersburg, MD) was implanted in the STN (3.6 mm posterior (P), 2.6 mm mediolateral (ML) from bregma; 6.6-6.9 mm dorsoventral (DV) from surface of brain). A cannula (23 gauge stainless steel needle, cut to 1.9 cm length) was placed in the MFB) 2.0 mm P, 2.0 mm ML from bregma; 8.5 mm from surface of skull). In addition, stainless steel bone screws (Fine Science Tools, item no. 19010-00) were used to secure the headcap, with one bone screw located above M1 (2.5 mm anterior, 2.5 mm ML from bregma) used to record the M1 ECoG. A bone screw located above the cerebellum was used as a reference. The stimulating microelectrode array and the ECoG contacts were connected to separate headstages (Omnetics, A79000) for subsequent connections to stimulating and recording cables. Rats were given an additional dose of meloxicam 24 h after the first dose and were monitored closely.

At one week post-implantation, rats were lesioned under 3.0-3.5% sevoflurane anesthesia to cause unilateral degeneration of dopaminergic neurons in the substantia nigra pars compacta (SNc). Sixty minutes before lesioning, the rats were pretreated with 50 mg/kg pargyline and 5 mg/kg desipramine injected intraperitoneally (i.p.). The 6-OHDA (Sigma-Aldrich; 5 mg 6-OHDA/3 mL 0.9% NaCl) solution was prepared immediately before use, and 10 μL was infused through the cannula at a rate of 1 μL/min Rats were left to recover at least one week before any additional measurements. Lesions were assessed via methamphetamine induced circling (see section 2.2 below), and circling of at least 3 turns/min in the direction ipsilateral to the lesion indicates >90% loss of dopaminergic neurons in the SNc. If this criterion was not met, rats were lesioned again, up to a total of three times, and secondary administrations were required in most rats.

There were two primary exclusion criteria for the implanted rats, decided a priori. The first was if the rats were not adequately lesioned after three separate attempts. The second was if the stimulation electrodes were improperly placed. Improper placement was determined if either the contact testing (see section 2.2) revealed no effective stimulation contacts or if the post-mortem histology (see section 2.6) revealed the electrode tips were outside the STN. Of the 30 rats, 15 were successful and used in this study, 4 were excluded because of failure to induce a 6-OHDA lesion, and 7 were excluded because of improper electrode placement. Additionally, 4 were excluded due to reaching humane endpoints that required euthanasia (2 rats had skin lesions, 1 had infection around the headcap, and 1 exhibited seizures following the 6-OHDA lesion).

Figures 5A, 5B, 5C:
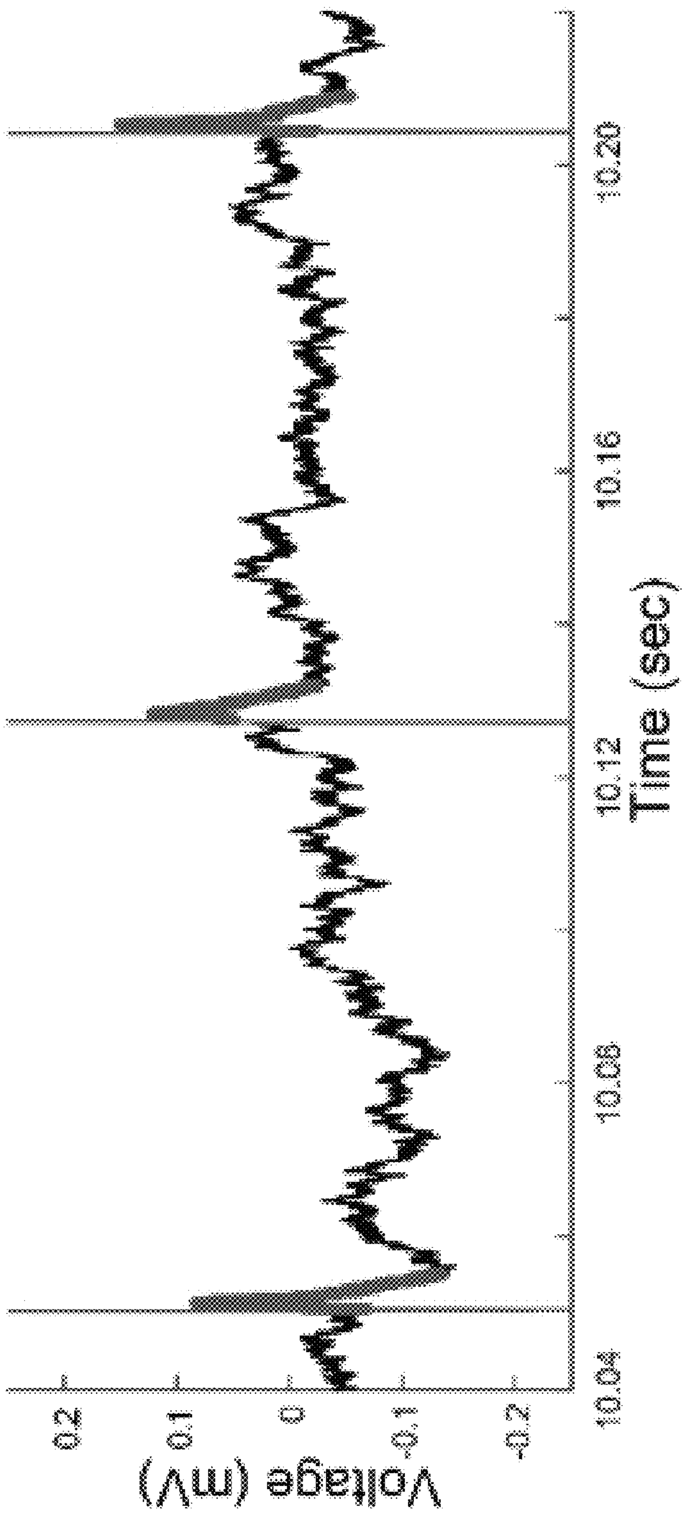
FIGS. 5A-5C: Short latency cortical evoked potentials (cEP) at different frequencies of STN DBS in 6-OHDA lesioned rats.

2.2 Electrical Stimulation. Stimulation was conducted using an isolated voltage to current convertor (A-M Systems) controlled by MATLAB (2020b, MathWorks, Natick, MA) or LabView (2017 SP1, National Instruments) software. Charge balanced biphasic pulses (pulse width 90 μs/phase when not specified) were applied at set stimulation frequencies. Bipolar stimulation was applied between two of the four electrodes. The stimulation amplitude and electrode contacts were determined for each rat before the start of experiments using a contact testing protocol based on sustained motor responses during 130 Hz stimulation, including increased contralateral turning, decreased ipsilateral turning, increased activity, and a lack of motor side effects including involuntary muscle contractions of the limbs and neck. Stimulation amplitudes typically varied between 50-100 μA. For all trials, unless otherwise specified, during the first five s of stimulation the amplitude was ramped up linearly to help reduce potential onset side effects. When possible, an alternating-phase method of stimulation was applied, wherein successive pulses alternated between cathodic phase-first and anodic phase-first stimulation (FIG. 5B). This inverted the stimulation artifact between successive pulses, and when the evoked potential was averaged over time, the artifact was removed and only the evoked potential remained. However, in some rats this method was less therapeutically effective than cathodic phase-first stimulation, in which case the more effective method was used.

2.3 Characterization of the cEP Across Stimulation Parameters. Simultaneous STN stimulation and ECoG recording were performed while the rats were in an awake, freely-moving state in their home cages to characterize changes in cEP features across stimulation conditions. In one set of experiments, four different stimulation frequencies (25, 75, 130, 200 Hz) were applied at four different amplitudes (0.4, 0.6, 0.8, 1.0 max amplitude) titrated to each rat's therapeutically effective amplitude determined during the contact testing protocol. In a second set of experiments, the same four stimulation frequencies were applied with three different pulse widths (60, 90, 120 μs) using each rat's therapeutically effective amplitude. In a third experiment, the same four stimulation frequencies were applied both in an awake state followed by an anesthetized state under 3.0-3.5% sevoflurane anesthesia, with the amplitude once again set to each rat's therapeutically effective amplitude and with rats anesthetized for at least 20 minutes before recordings began. For all three of these experiments, the conditions were randomized, the recordings were 3 min long, and there was a 5 min washout period between trials. Due to the low variability of the cEP within animals, each of these experiments were performed only once for each animal.

In a subset of rats, a probe-pulse stimulation technique was performed to measure cEPs. Two superimposed stimulation trains were applied, a first functional stimulation train that could have varying stimulation frequencies and amplitudes, and a second probe stimulation train at a lower frequency with fixed stimulation parameters. This probe-pulse train was set at a subharmonic of the first functional train so that the probe-pulses simply replaced those of the functional train. In offline analysis, the cEPs evoked from the probe-pulses were then quantified, enabling the determination of any functional changes in cEP features due to the different stimulation conditions. This technique was used with four stimulation frequencies (13, 75, 130, 200 Hz) and three amplitudes (60%, 80%, 100%), titrated to each rat's therapeutically effective amplitude. A probe-pulse frequency of 13 Hz was used, and the subharmonic closest to 13 Hz was selected for the probe pulses (e.g., for 75 Hz, every $6^{th}$ pulse was a probe pulse), with the probe pulse set to 100% amplitude. This technique was used during methamphetamine induced circling (see section 2.4) to assess symptom reduction.

In another set of experiments, the refractory period of the cEP was quantified. While rats were in an awake, freely-moving state, a paired-pulse stimulation protocol was delivered using inter-pulse intervals (IPIs) of (0.5, 0.75, 1, 1.25, 1.5, 1.75, 2, 3, 4, 5, 15, 50, 100, and 1000 ms), with one sec between the start of each pair of stimuli, and a total of 120 stimuli pairs applied over 2 min. The order of each 2 min stimulation epoch was randomized, and a 5 min washout period elapsed between epochs. The cEP magnitudes of the second pulses in each pair, normalized to the cEP magnitude at 1 Hz, were then fit by a sigmoid, $$y = \frac{1}{1 + e^{(t50-t)*slope}}$$

to determine the refractory period of the cEP. Each experiment was performed once in each animal using stimulation contacts and amplitude chosen during the contact test to be therapeutically effective.

2.4 Behavioral Tests. Simultaneous STN stimulation and ECoG recordings were conducted during behavioral tests at different stimulation frequencies to determine the correlation between various biomarkers and changes in symptoms. Seven different stimulation frequencies were used (13, 25, 50, 75, 100, 130, 200 Hz), with individual frequencies selected to span a range of known behavioral efficacies and not to fall on harmonics of 60 Hz. In one animal, a different set of stimulation frequencies was used: 10, 20, 30, 50, 60, 75, 100, 115, 130 Hz. The results from this animal were included in the correlation analysis but were not used in the characterization of the cEP over time.

Two different behavioral tests were used to assess symptoms: methamphetamine induced circling and an adjusting steps task. For the circling task, rats were given a single injection of methamphetamine (1.875 mg/kg in 0.9% saline, i.p.) 20 min prior to placement in a cylinder. The cylinder was placed in a dark chamber and an infrared camera was used to capture the rat behavior. A rotating electrical commutator (PlasticsOne) was used to prevent cable twisting. The behavioral effects of DBS were quantified using randomized blocks of the seven different stimulation frequencies. Each stimulation frequency was repeated at least three different times, with 60 s stimulation epochs spaced 120 s apart. Circling behavior was video recorded and tracked using behavioral analysis software (Clever Systems, Reston, VA). The angular velocity and distance travelled per minute (linear speed) were calculated offline from the tracking data using MATLAB. The normalized angular velocity and linear speed for each trial were calculated by dividing the average angular velocity or linear speed during the stimulation-on period by the average angular velocities or linear speeds during the 60 s pre-stimulation-off and post-stimulation-off periods immediately before and after each stimulation-on period. The normalized angular velocities and linear speeds for each stimulation rate were then averaged across all randomized blocks.

Deficits in contralateral limb use were quantified via a forelimb adjusting steps task, which is a validated measure of parkinsonian akinesia in rats. Rats were held with their hind limbs elevated and pulled backward at a steady rate over a 1-meter glass runway (Runway, CleverSys). Each epoch consisted of 3-5 trials across the runway. The movement was video recorded from below and analyzed offline by counting the number of adjusting steps taken with each forelimb. All offline analysis of the video recordings was blinded to the stimulation conditions. Behavioral efficacy of DBS was quantified by taking the ratio of the number of contralateral steps to the number of ipsilateral steps. Each of the seven stimulation frequencies, as well as a no stimulation control, were applied in random order before and during each adjusting steps session. Stimulation was delivered for five min before each epoch began and continued through the epoch. A five min no-stimulation washout period elapsed between stimulation epochs. The five min of recording data before each stepping epoch began, and during which the rat was stimulated but left in an awake, freely moving state, was also used on its own to quantify changes in the cEP over time (section 3.1) and to quantify the change in spectral biomarkers between baseline and 130 Hz stimulation (section 3.2). When possible, multiple (typically 1-3) methamphetamine induced circling and adjusting steps experiments were performed in each rat, with the behavioral score and biomarker values first averaged across all replicates of each stimulation condition before quantifying their correlations.

2.5 Electrophysiological Recording and Analysis. The ECoG signal was sampled at either 20 or 100 kHz using a multichannel acquisition processor system (Plexon Inc, Dallas, TX) with a 50× gain. Four biomarkers were quantified offline using custom scripts in MATLAB: beta band power, beta band bursting, phase-amplitude coupling (PAC), and the average cEP from 0-5 ms post-stimulation. From the average cEP profiles, the value and latency of the short-latency cEP peak was measured using MATLAB's findpeaks function within the range of 1-3 ms post-stimulus. The magnitude was then quantified, defined as the range in mV from the cEP peak to the point 5 ms post-stimulus. This measure of magnitude, as opposed to simply the peak value, was more reliable as it was less affected by noise, and has also been used to quantify human cEP magnitude.

For each spectral measurement, the stimulation artifacts were blanked, data was down-sampled to 1 kHz, and the baseline was subtracted. Artifact blanking was performed using a Gaussian weighting scheme implemented over the 100 nearest stimulation artifact templates. Spectral power (13-30 Hz) was calculated using the mtspectrumc function from the Chronux MATLAB package (chronux.org). The power was quantified in six different bands: theta (4-8 Hz), alpha (3-13 Hz), low-beta (13-20 Hz), high-beta (20-30 Hz), beta (13-30 Hz), and gamma (30-50 Hz). Power was then normalized to the broadband power from 4-90 Hz. To quantify PAC, the modulation index (MI) was calculated using a known method (e.g., Onslow, Bogacz et al. 2011), with phase frequencies of 1-30 Hz and amplitude frequencies from 10-200 Hz. The PAC was then subdivided into ten distinct phase/amplitude regions (Table 2), with individual boundaries selected based on the observed regions of strongest coupling across animals. Within each region, the average value of the ten highest MIs within that region was quantified. Beta band bursting was calculated using a known method (e.g., Tinkhauser, Pogosyan et al. 2017), performing bandpass filtering within set frequency bands (theta 4-8 Hz; alpha 8-13 Hz; low-beta 13-20 Hz; high-beta 20-30 Hz), applying the Hilbert transform, and then using a 75% threshold to quantify bursting behavior, thus accounting for changes in overall signal power. Using this method, both the mean and $90^{th}$ percentiles of the beta burst amplitude and durations were quantified. The value of the 75% threshold itself was also tracked, as it serves as a metric of overall power in that band.

2.6 Histology. After the completion of experiments (2-6 months post-implant), rats were deeply anesthetized with urethane (1.8 g/kg, i.p.) and perfused transcardially with 0.1M phosphate buffered saline (PBS) followed by 4% paraformaldehyde in 0.1M PBS. The brain was post-fixed overnight in 4% paraformaldehyde and then transferred to 30% sucrose. The brains were frozen in optimal cutting temperature compound and cut into 50 μm sections in either the coronal or horizontal planes using a cryostat (CM3050S, Leica Microsystems) and processed for two sets of staining:

tyrosine hydroxylase (TH) and cresyl violet. TH immunohistochemistry was used to determine the extent of degeneration of dopaminergic neurons in the SNc and to visualize electrode locations. Briefly, after three rinses in PBS, brain sections were first incubated for 10 min in 3% hydrogen peroxide. The sections were rinsed and blocked for 1 h at room temperature in blocking solution containing 10% goat serum. The sections were then incubated in anti-tyrosine hydroxylase antibody (AB152; 1:1000, Vector Laboratories) overnight at 4° C. in PBS with 10% goat serum and 0.25% Trion X-100. After three rinses in PBS, the sections were incubated with biotinylated goat antirabbit secondary antibody (BA-1000, 1:250, Vector Laboratories) with 10% goat serum and 0.25% Trion X-100 in PBS for 1 h at room temperature. After rinsing, the sections were incubated in a VECTASTAIN Elite ABC kit (Vector Laboratories) solution for 1 h and then visualized using DAB solution. Cresyl violet counter staining was used to help verify electrode locations compared with a rat brain atlas.

2.7 Experimental Design and Statistical Analysis. All statistical tests were performed in JMP Pro 15.1 (SAS Institute Inc.) and incorporated the animal number as a random effect to account for repeated measures when applicable. In the first set of experiments, the effects of three variables (stimulation amplitude, pulse width, and anesthesia) were characterized on the cEP magnitude and latency at different stimulation frequencies. For each variable a repeated measures multiple regression analysis was performed, quantifying the effects of the variable, stimulation frequency, and the interaction of the variable with stimulation frequency. In a second set of experiments, the cEP magnitude over time was fit to linear and exponential models and their model fits were compared using the Akaike Information Criteria corrected (AICc) weights. Repeated measures linear regression was then performed on each term of the exponential models for each animal at each stimulation frequency. In another set of experiments, changes in spectral features were characterized between 0 and 130 Hz DBS, which were quantified using paired t-tests. Finally, the Pearson's product-moment correlation (PPMC) of five different biomarkers was quantified with two behavioral measurements of symptom reduction. All results are presented as mean±standard error and were considered significant at $p<0.05$. Study data are available at the Duke Digital Repositories under DOI 10.7924/r4r78d86s.

5. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Deep brain stimulation (DBS) of the subthalamic nucleus (STN) antidromically activates the motor cortex (M1), and this cortical activation appears to play a role in the treatment of hypokinetic symptoms. The synchronous antidromic activation takes the form of a short-latency cortical evoked potential (cEP) in electrocorticography (ECoG) recordings of M1. The utility of the cEP as a biomarker for STN DBS was assessed in unilateral 6-hydroxydopamine lesioned female Sprague Dawley rats, with stimulating electrodes implanted in the STN and the ECoG recorded above M1. The correlations of the cEP magnitude and latency with symptom reduction from DBS were quantified and compared to the correlation between symptoms and several commonly used spectral-based biomarkers. The cEP features correlated strongly with symptom reduction and were highly consistent across animals, while the spectral biomarkers correlated weakly with symptom reduction and were highly variable across animals. The cEP is thus a useful biomarker for assessing the therapeutic efficacy of DBS parameters, as its features strongly correlate with symptom reduction, it is consistent across time and subjects, it can be recorded under anesthesia, and it is simple to quantify with a large signal-to-noise ratio, enabling rapid, real-time evaluation. Among other aspects, the results provided herein provide further evidence that antidromic cortical activation mediates symptom reduction from STN DBS and that the dependence of symptom reduction on stimulation frequency may be related to antidromic spike failure.

Cortical Response to Variations in STN DBS Parameters. The magnitude and latency of the cEP were quantified during DB S with four stimulation frequencies (25, 75, 130, 200 Hz) at four different amplitudes (0.4, 0.6, 0.8, 1.0 max amplitude) (FIG. 6A), and a repeated measures multiple regression was performed (Table 2, n=6). Higher stimulation frequencies decreased the cEP magnitude and increased the cEP latency. Additionally, higher stimulation amplitudes increased the cEP magnitude but had no effect on cEP latency. Also, there was a significant interaction between stimulation frequency and amplitude on the cEP magnitude, but not the cEP latency, indicating that at higher stimulation frequencies there was a smaller absolute effect of stimulation amplitude. However, when the cEP magnitudes at each amplitude were normalized to their value at the lowest stimulation frequency (25 Hz), there was no longer an effect of stimulation amplitude (Table 2), indicating that although stimulation amplitude affects the absolute reduction in cEP magnitude at high stimulation frequencies, it does not affect its relative change with frequency.

TABLE 2 cEP Characterization Statistics.

| | | Normalized | | cEP Magnitude | | | cEP Latency | | |
|---|---|---|---|---|---|---|---|---|---|
| Condition | N | By | Variable | B | t | P | B | t | P |
| Amplitude | 6 | Single Condition | Frequency | −3.0E−03 | −20.31 | *<.0001 | 0.002 | 16.27 | *<.0001 |

TABLE 2-continued cEP Characterization Statistics.

| Condition | N | Normalized By | Variable | cEP Magnitude B | cEP Magnitude t | cEP Magnitude P | cEP Latency B | cEP Latency t | cEP Latency P |
|---|---|---|---|---|---|---|---|---|---|
| | | | Amplitude | 0.611 | 15.06 | *<.0001 | 0.030 | 0.96 | 0.3423 |
| | | | Freq*Amp | −4.4E−03 | −6.85 | *<.0001 | 1.0E−04 | 0.21 | 0.8346 |
| | | Each Condition | Frequency | −4.2E−03 | 24.18 | *<.0001 | 1.8E−03 | 16.98 | *<.0001 |
| | | | Amplitude | −3.1E−03 | −0.06 | 0.9498 | 1.7E−03 | 0.06 | 0.955 |
| | | | Freq*Amp | −6.4E−05 | −0.08 | 0.934 | 3.4E−05 | 0.07 | 0.9418 |
| Pulse Width | 5 | Single Condition | Frequency | −3.3E−03 | 19.46 | *<.0001 | 1.3E−03 | 9.47 | *<.0001 |
| | | | Pulse Width | 4.3E−03 | 9.48 | *<.0001 | 6.5E−04 | 1.77 | 0.0824 |
| | | | Freq*PW | −6.8E−05 | −4.02 | *0.0002 | 7.6E−07 | 0.13 | 0.8938 |
| | | Each Condition | Frequency | −4.1E−03 | 20.31 | *<.0001 | 1.3E−03 | 9.35 | *<.0001 |
| | | | Pulse Width | 3.8E−04 | 0.72 | 0.4756 | −1.4E−04 | −0.37 | 0.7094 |
| | | | Freq*PW | −4.9E−07 | −0.06 | 0.9525 | −3.5E−08 | −0.01 | 0.9953 |
| Sevoflurane | 6 | Single Condition | Frequency | −3.2E−03 | 14.38 | *<.0001 | 1.3E−03 | 5.03 | *<.0001 |
| | | | Sevoflurane | 0.140 | 9.69 | *<.0001 | −9.2E−02 | −5.67 | *<.0001 |
| | | | Freq*Sevo | −1.1E−03 | −5.01 | *<.0001 | 9.2E−05 | 0.37 | 0.7132 |
| | | Each Condition | Frequency | −4.3E−03 | 14.93 | *<.0001 | 1.2E−03 | 5.43 | *<.0001 |
| | | | Sevoflurane | 8.2E−03 | 0.44 | 0.6624 | 3.0E−02 | 2.16 | *0.0368 |
| | | | Freq*Sevo | −1.2E−05 | −0.04 | 0.9668 | 1.9E−04 | 0.92 | 0.3640 |

The cEP amplitude and latency were quantified during DBS with three different pulse widths (60, 90, 120 us) at four different stimulation frequencies (13, 75, 130, 200 Hz) (FIG. 6B), and a multiple regression was performed (repeated measures multiple regression, n=4, Table 2). Similar to the cEP amplitude, there were significant effects of frequency, pulse width, and frequency×pulse width on the cEP magnitude, but only a significant effect of frequency on the cEP latency. Additionally, when the cEP magnitude at each pulse width was normalized to its value at 25 Hz there was no longer a significant effect of pulse width.

Figures 6A, 6B, 6C:
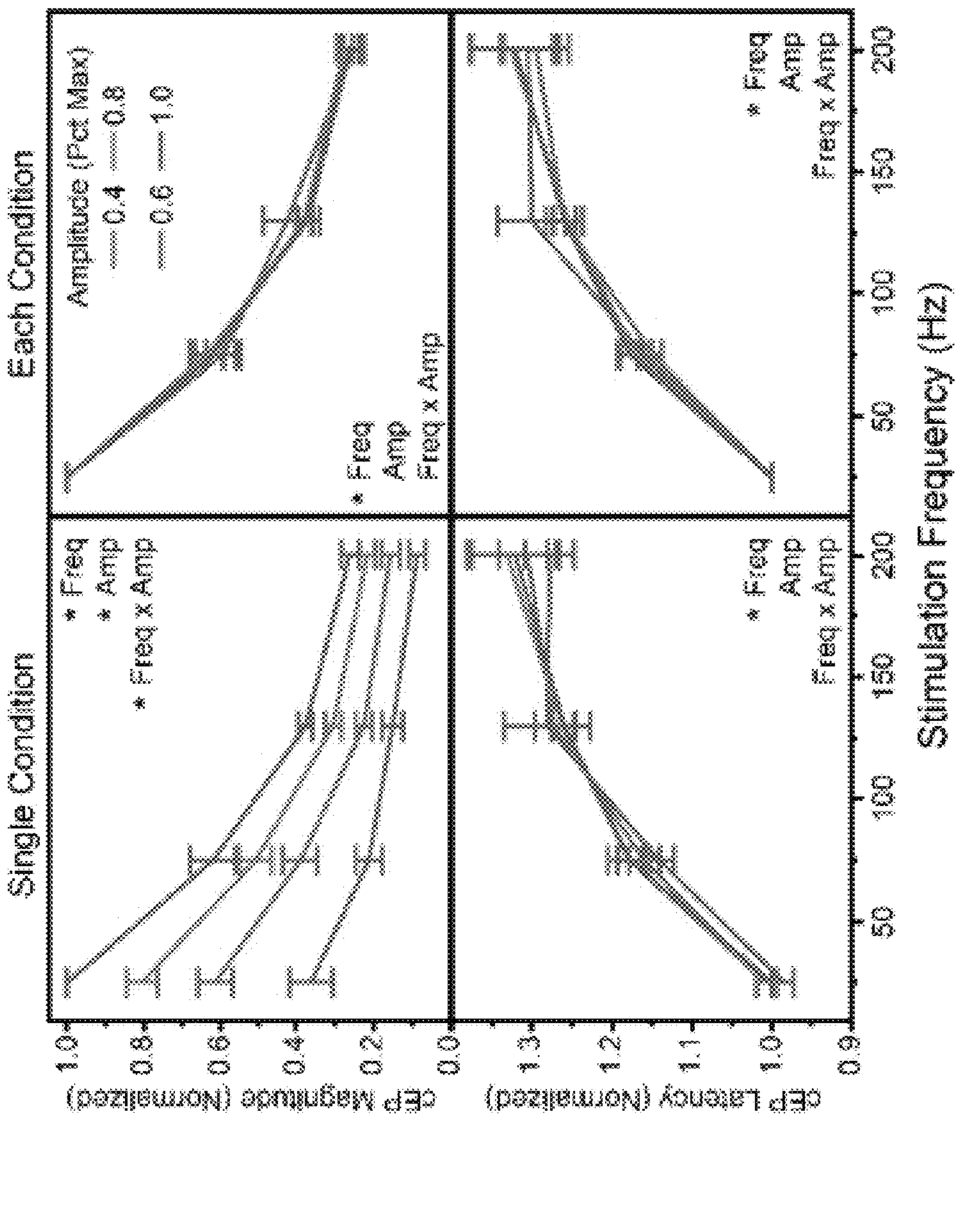
FIGS. 6A-6C: Changes in cEP magnitude and latency at four different stimulation frequencies (25, 75, 130, 200 Hz) during different stimulation conditions. The left column of each panel is normalized for each animal to the 25 Hz value of a single condition, while the right column of each panel is normalized to the 25 Hz value of each condition. For each group a repeated measures multiple regression analysis was performed (Table 2). cEP magnitude and latency as a function of stimulation frequency and amplitude (as a percentage of each rat's therapeutically effective amplitude) (n=6) are shown in FIG. 6A. Data in the Single Condition group is normalized to the 1.0 Amp value. For the Single Condition group, there were significant effects of frequency, amplitude, and freq*amp on the cEP magnitude, but only a significant effect of frequency on the cEP latency. However, for the Each Condition group there was only a significant effect of frequency on both the cEP magnitude and latency.
Figures 6A, 6B, 6C:
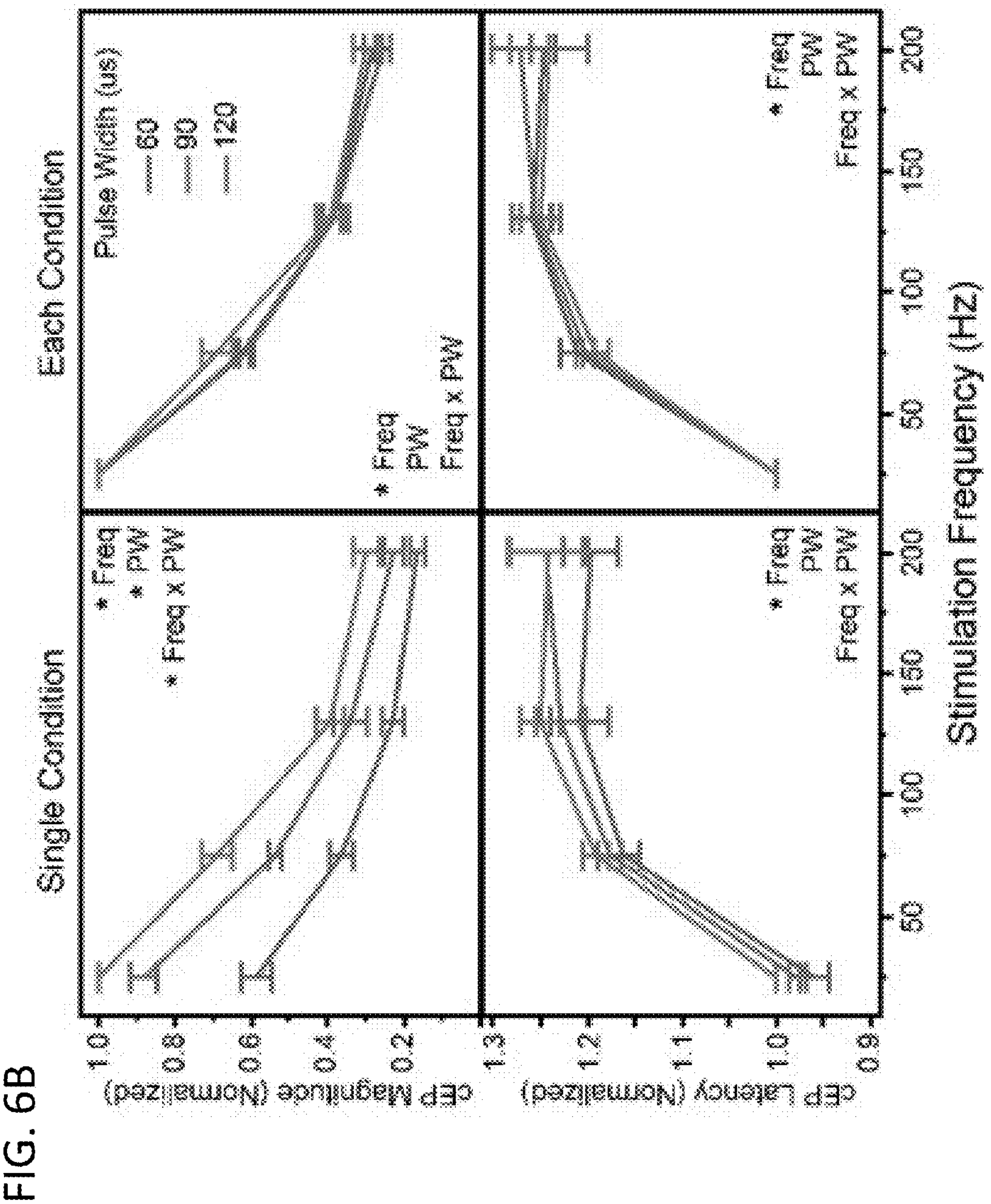
Figures 6A, 6B, 6C:
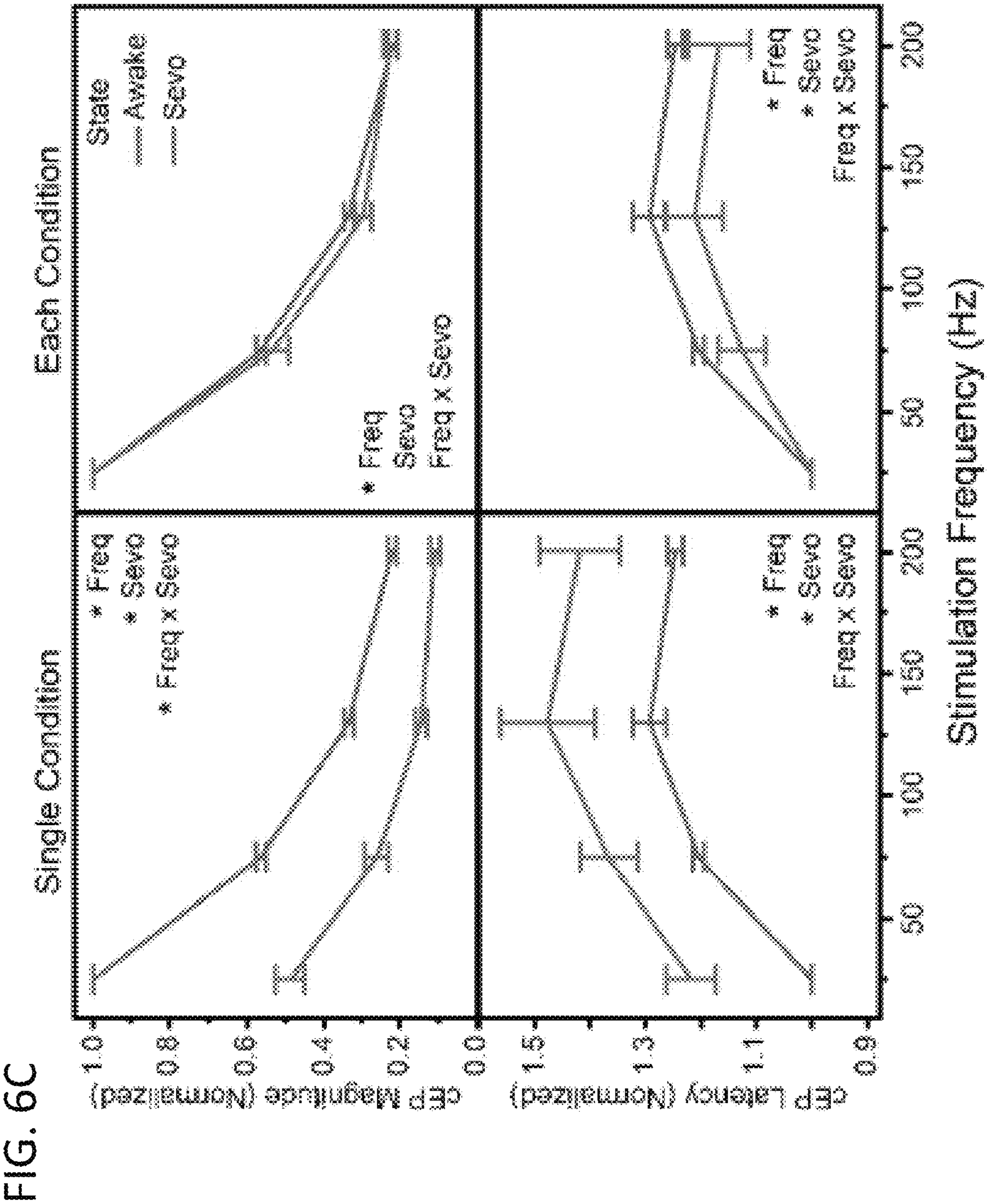

The effect of sevoflurane anesthesia on the cEP were quantified. Four different stimulation frequencies were applied (25, 75, 130, and 200 Hz) while the rats were in an awake, freely-moving state, and following these recordings, rats were anesthetized for at least 20 minutes under 3.0-3.5% Sevoflurane before a second round of recordings (FIG. 6C). There were effects of stimulation frequency and sevoflurane, with sevoflurane reducing the cEP magnitude and increasing its latency (repeated measures multiple regression, n=6, Table 2). Additionally, there was a significant interaction term between stimulation frequency and sevoflurane on the cEP magnitude but not the cEP latency, indicating that sevoflurane caused a smaller absolute reduction in cEP magnitude at high stimulation frequencies. However, similar to the effects of stimulation amplitude and pulse width, when the cEP magnitude was normalized to its value at the lowest stimulation frequency (25 Hz), there was no longer a significant effect of sevoflurane or interaction between stimulation frequency and sevoflurane. Thus, sevoflurane led to a smaller absolute reduction in cEP magnitude at high frequencies but did not change the relative reduction in cEP magnitude.

The refractory period of the cEP (FIG. 7) was determined as $t_{50}$=0.985 ms (n=5), which made clear that the change in cEP magnitude at higher stimulation frequencies was not due to neuronal refractoriness. In addition to the refractory period, there was also a hyperexcitable interval between approximately 5-10 ms, which corresponds to stimulation frequencies from 100-200 Hz.

Five-minute recordings of the cEP were analyzed at different stimulation frequencies while the rat was in an awake, freely-moving state to quantify how the cEP magnitude changed over time (n=7). It appeared that there was an exponential decay in the cEP magnitude for stimulation frequencies ≥50 Hz (FIG. 8A), and to test this, the average cEP magnitude was quantified at six different time points (5, 10, 30, 60, 120, 300 s) at each stimulation frequency (FIG. 9A), normalized to the peak cEP magnitude in each animal. Linear and exponential fits were compared at each stimulation frequency using the AICc Weights. The 13 and 25 Hz stimulation were best fit linearly, while stimulation frequencies ≥50 Hz were best fit with an exponential decay (Table 3).

TABLE 3

Exponential vs. Linear Fits of cEP Magnitude.

| Frequency | N | Model Fit | AICc | AICc Weight |
|---|---|---|---|---|
| 13 Hz | 7 | Linear | −125.83329 | 0.602 |
| | | Exponential | −125.00473 | 0.398 |
| 25 Hz | 7 | Linear | −78.701648 | 0.676 |
| | | Exponential | −77.232482 | 0.324 |
| 50 Hz | 7 | Linear | −75.853155 | 0.074 |
| | | Exponential | −80.906623 | 0.926 |
| 75 Hz | 7 | Linear | −62.473505 | 0.000 |
| | | Exponential | −81.514918 | 1.000 |
| 100 Hz | 7 | Linear | −58.251364 | 0.000 |
| | | Exponential | −99.14181 | 1.000 |
| 130 Hz | 7 | Linear | −50.651149 | 0.000 |
| | | Exponential | −93.276194 | 1.000 |
| 200 Hz | 7 | Linear | −65.235884 | 0.000 |
| | | Exponential | −101.51872 | 1.000 |

To characterize further the cEP magnitude during high frequency DBS (≥50 Hz), the cEP magnitude was quantified for each animal and stimulation frequency as a function of time, averaged in 500 ms windows, and fit it with an exponential decay model of $$y = a * \exp\left(-\frac{x}{\tau}\right) + c$$

Figures 9A, 9B, 9C, 9D:
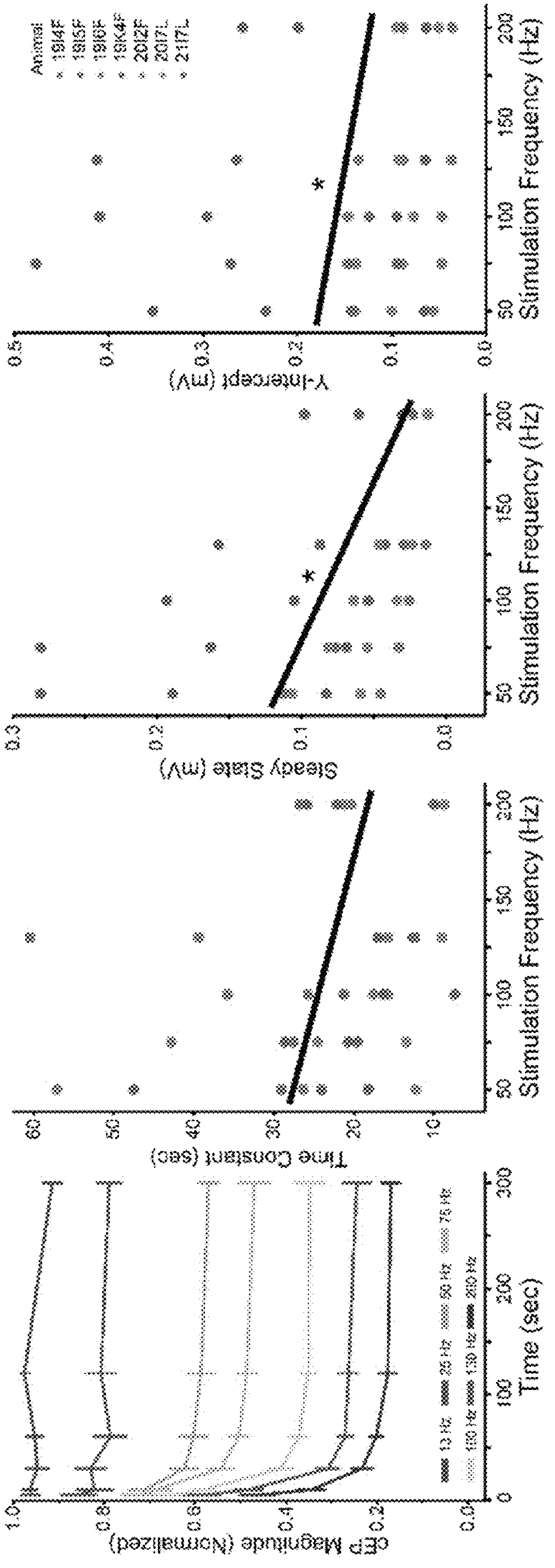
FIGS. 9A-9D: Statistical analysis of the change in cEP magnitude over time.

(FIG. 8B). The first five s of each trial were excluded from the analysis because a five s ramp-up of stimulation amplitude was applied at the beginning of each trial. Three terms were analyzed: the y-intercept (a+c), the steady state value (c), and the time constant ($\tau$) (FIGS. 9B-9D). The effect of stimulation frequency on each term was quantified using repeated measures linear regression (n=7, Table 4).

TABLE 4

Temporal Analysis of cEP Magnitude.

| Term | N | B | t | p |
|---|---|---|---|---|
| a + c | 7 | −3.61E-04 | −3.49 | *0.0129 |
| c | 7 | −5.89E-04 | −4.05 | *0.0067 |
| $\tau$ | 7 | −6.20E-02 | −2.14 | 0.0761 |

Higher stimulation frequencies reduced both a+c and c, but not $\tau$(28.1±4.3 s). The change in c is unsurprising, as it corresponds to the steady state changes in cEP magnitude observed previously. However, the change in a+c was unexpected, as it indicates that with higher stimulation frequencies the predicted y-intercept decreases. Because the first five s in the analysis were excluded, what occurs during that time is somewhat unclear. However, refractory period experiments indicated that the true y-intercepts for these stimulation frequencies should all be approximately the same, so this observation indicates that, in addition to the long-term changes in cEP magnitude that occur from 5-300 s, there is likely an additional short-term change that occurs over the first five s that is also affected by stimulation frequency. The difference in timing of these stages may indicate multiple mechanisms causing the reduction in cEP magnitude, such as conduction failure of action potentials at the branch point, submyelin accumulation of potassium along the main axon, or invasion failure at the soma. The cEP latency exhibits a similar long-duration change over time, although curve-fitting was not performed due to the cEP latency generally having far greater variability over time than the cEP magnitude.

Example 2

Figure 10:
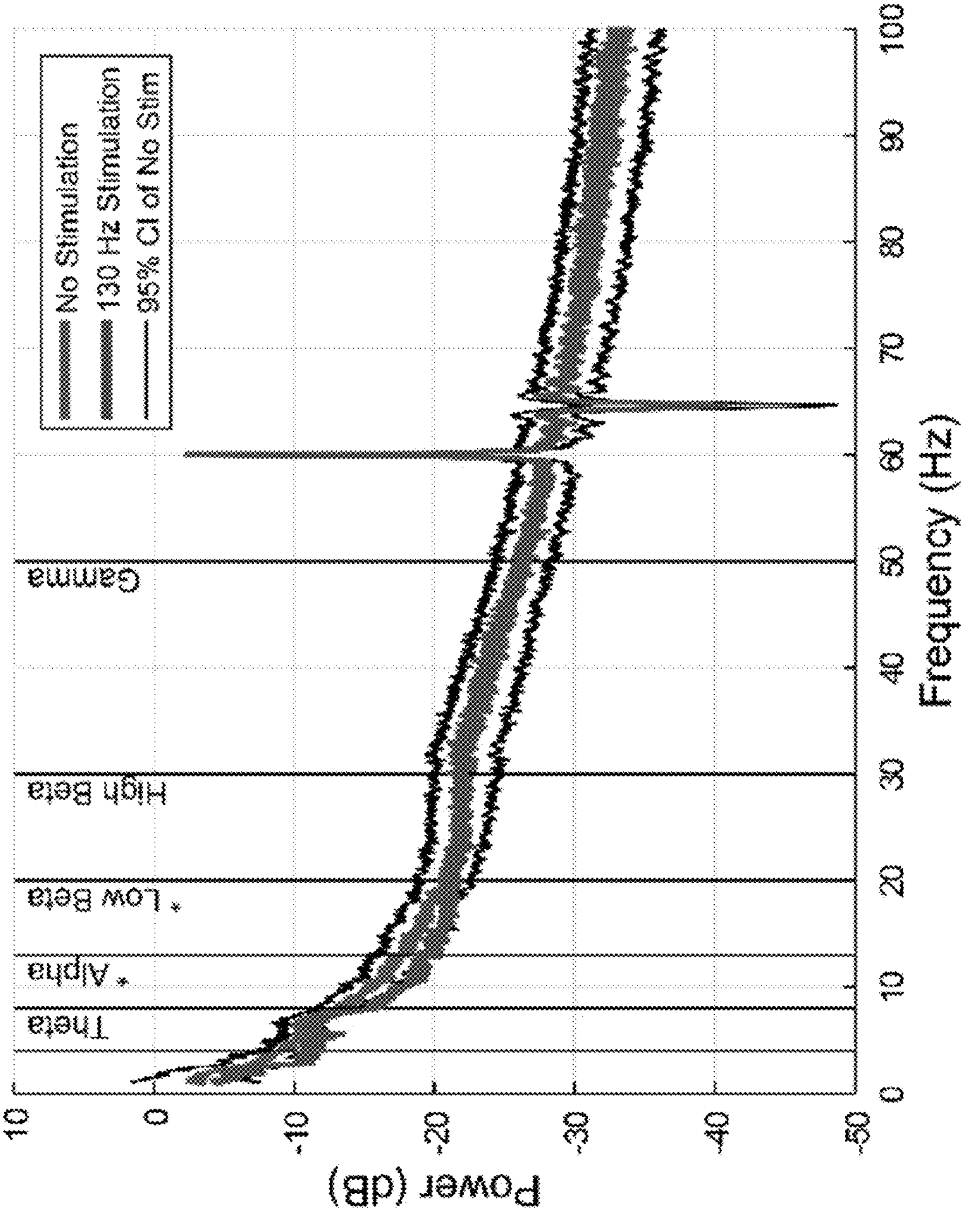
FIG. 10: Average spectral power during five-minute recordings while rats were in an awake, freely moving state (n=11) either with no stimulation (red) or with 130 Hz stimulation (blue). The 95% confidence interval for the no stimulation group is in black. Spectra were normalized to the broadband power from 4-90 Hz. The deflection at 65 Hz is due to the stimulus artifact removal. Performing a paired t-test of the effect of 130 Hz DBS in individual frequency bands shows a significant reduction in power in the alpha (8-13 Hz), and low beta (13-20 Hz) bands, but not in the theta (4-8 Hz), high beta (20-30 Hz) or gamma (30-50 Hz) bands (n=11, Table 6).

Properties of Cortical Spectral Biomarkers. Three spectral-based biomarkers were quantified from cortical recordings: the power spectrum, spectral bursting, and PAC. No stimulation and 130 Hz DBS were compared using five minute recordings during an awake, freely-moving state (n=11). For the no stimulation trials, artifact subtraction was performed using the artifact times from the 130 Hz trials to ensure that the artifact blanking method was not contributing to any changes. The power spectra (FIG. 10) exhibited a pronounced peak at approximately 7 Hz, as well as a peak in the high-beta range. DBS at 130 Hz reduced the low frequency power in the alpha (8-13 Hz) and low-beta (13-20 Hz) bands (paired t-test, n=11, Table 4). There was no significant change in the theta (4-8 Hz), high-beta (20-30 Hz), or gamma (30-50 Hz) bands across animals, although a few animals did have prominent high-beta peaks that were modulated by DBS.

TABLE 5

Power Spectrum Paired t-Test Statistics.

| Band | Frequency (Hz) | DF | t | p |
|---|---|---|---|---|
| Theta | 4-8 | 10 | 1.66 | 0.129 |
| Alpha | 8-13 | 10 | 2.82 | *0.018 |
| Low Beta | 13-20 | 10 | 2.38 | *0.038 |
| High Beta | 20-30 | 10 | 0.11 | 0.914 |
| Gamma | 30-50 | 10 | −1.95 | 0.080 |

Figure 11:
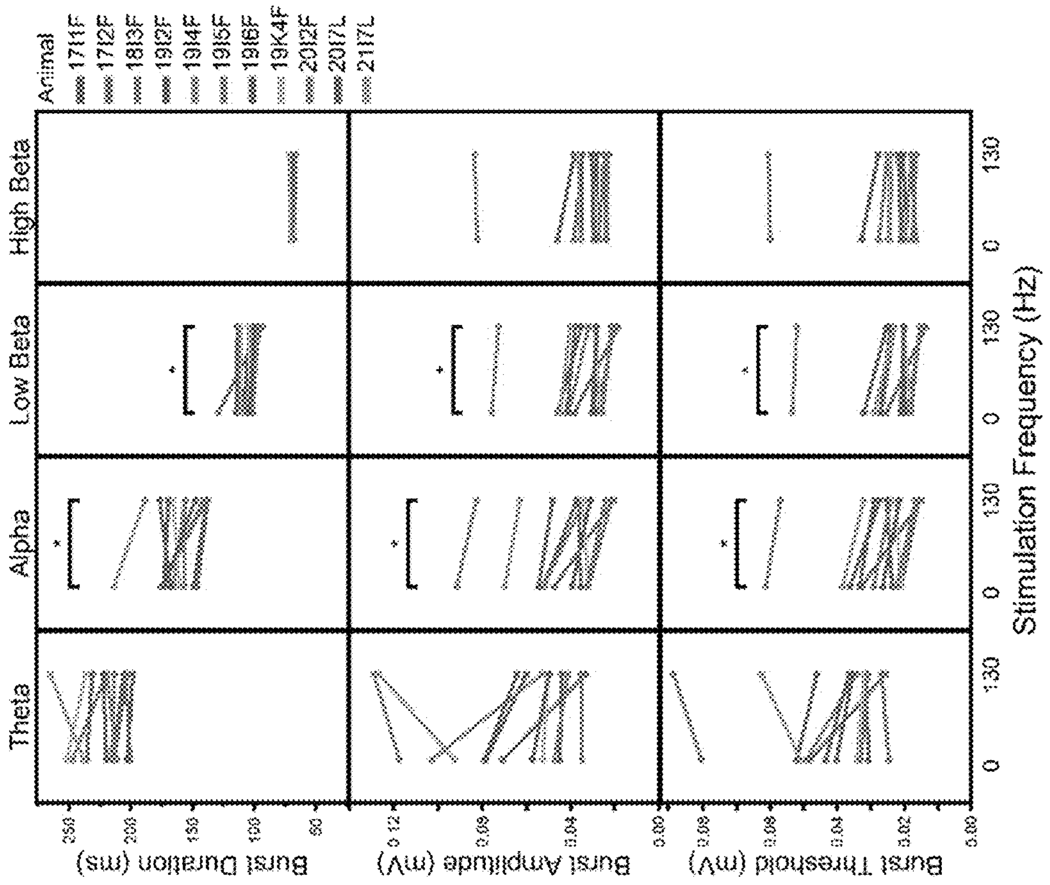
FIG. 11: Spectral bursting characteristics during five-minute recordings while rats were in an awake, freely moving state (n=11) either with no stimulation or with 130 Hz DBS. Bursting characteristics were quantified for four bands: theta (4-8 Hz), alpha (8-13 Hz), low beta (13-20 Hz) and high beta (20-30 Hz). In each band, the average burst duration (top), average burst amplitude (middle), and 75% burst threshold (bottom) were quantified. A paired t-test of the effect of stimulation on each metric in each band showed a significant effect of stimulation for all three metrics in the alpha and low beta bands, but not in the theta or high beta bands (n=11, Table 6).

Bursting in the beta band in the human STN is a potential biomarker for closed-loop DBS, and whether similar bursting was present in the rat M1 ECoG was quantified. Bursting in the theta (4-8 Hz), alpha (8-13 Hz), low-beta (13-20 Hz), and high-beta (20-30 Hz) bands were quantified, measuring the average burst duration and amplitude, as well as the 75% threshold (FIG. 11). There was a reduction in all three features during 130 Hz DBS, but only in the alpha and low-beta bands (paired t-test, n=11, Table 6). No change in any bursting feature in the theta or high-beta bands was detected.

TABLE 6

Spectral Bursting Paired t-Test Statistics.

| Frequency | | Burst Duration | | Burst Amplitude | | Burst Threshold | |
|---|---|---|---|---|---|---|---|
| (Hz) | DF | t | P | t | P | t | P |
| 4-8 | 10 | 0.68 | 0.512 | 0.900 | 0.392 | 1.150 | 0.276 |
| 8-13 | 10 | 2.73 | *0.021 | 3.280 | *0.008 | 3.500 | *0.006 |
| 13-20 | 10 | 2.55 | *0.029 | 2.910 | *0.016 | 3.140 | *0.011 |
| 20-30 | 10 | 1.36 | 0.204 | 0.570 | 0.581 | 0.810 | 0.438 |

Figures 12A, 12B, 12C:
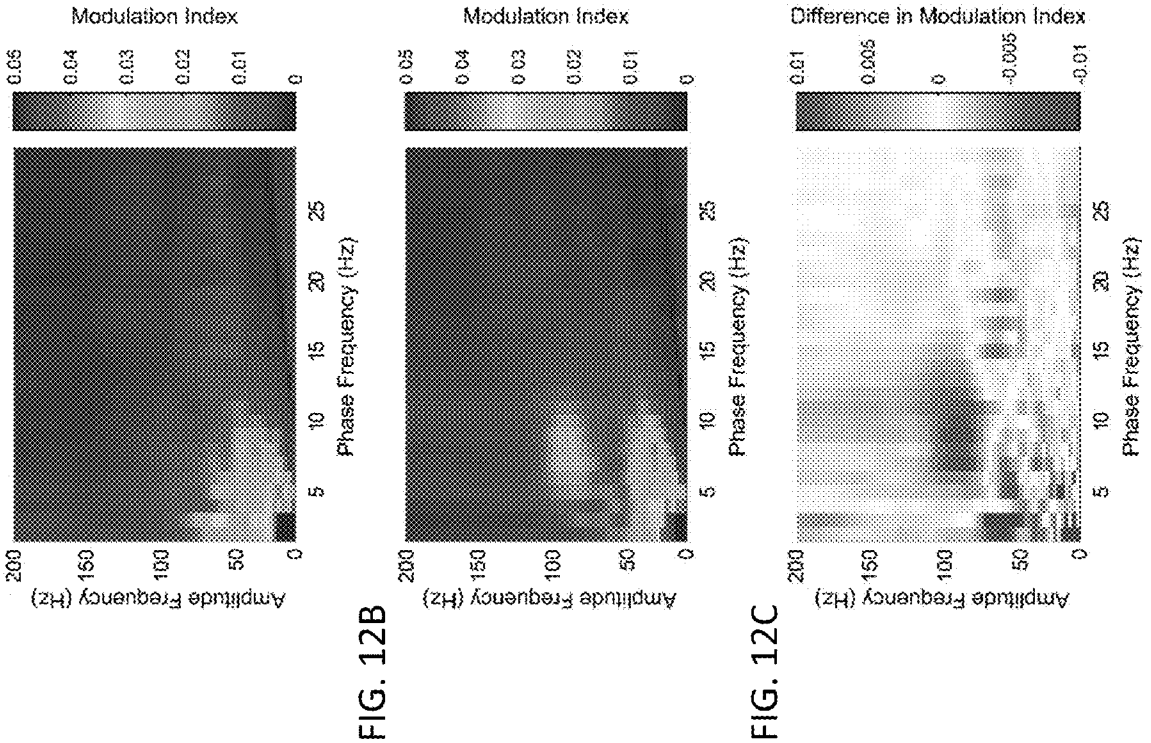
FIGS. 12A-12C: Representative data from phase-amplitude coupling (PAC) during five-minute recordings while rats were in an awake, freely moving state (n=11) either with no stimulation (FIG. 12A) or with 130 Hz DBS (FIG. 12B). The color bar represents the average modulation index for each phase/amplitude pair across all animals FIG. 12C includes the average difference in modulation index between no stimulation and 130 Hz stimulation across animals. Across animals, DBS appears to decrease coupling in the low-phase, low-amplitude region (phase 1-5 Hz, amplitude 10-50 Hz) and increase coupling in the alpha, high-amplitude region (phase 8-13 Hz, amplitude 75-120 Hz). Binning the PAC into ten subregions and quantifying the effect of stimulation revealed a significant difference only in the High-Amplitude region (phase 1-30 Hz, amplitude 75-200 Hz) (paired t-test, n=11, Table 7).

Also, the cortical PAC was quantified, which is an informative cortical biomarker in humans. The average PAC across the five minute trials was quantified for phase frequencies 1-30 Hz and amplitude frequencies 10-200 Hz (FIG. 12). In the baseline case there were two common regions of increased coupling: a low-phase, low-amplitude region with phase <10 Hz and amplitude <50 Hz, and a low-phase, high-amplitude region with phase <20 Hz and amplitude >50 Hz. However, there was substantial variation across animals, with some exhibiting far less coupling than others. A 130 Hz DBS caused changes in coupling in most animals, but the specific subregions that changed were inconsistent across animals. When looking at the average difference in PAC across animals (FIG. 12C), there was a general decrease in theta/low-amplitude coupling and increase in alpha/high-amplitude coupling, but this was primarily due to a few outlier animals and was not present across all. To determine whether there were any consistent changes, the ten highest PAC MI values were averaged in ten different sub-regions (Table 7), and it was found that the only subregion with a significant change from stimulation was the High-Amplitude region (phase 1-30, amplitude 75-200), which had an increase in PAC with DBS (paired t-test, n=11, Table 7). However, this effect was largely driven by a few animals and was not present in all.

TABLE 7

PAC Regions and Paired t-Test Statistics.

| Region | Phase(Hz) | Amplitude (Hz) | DF | t | p |
|---|---|---|---|---|---|
| All | 1-30 | 30-200 | 10 | 0.39 | 0.705 |
| Theta | 1-8 | 10-50 | 10 | −0.10 | 0.190 |
| Alpha/Beta | 8-20 | 50-200 | 10 | −1.41 | 0.190 |

TABLE 7-continued

PAC Regions and Paired t-Test Statistics.

| Region | Phase(Hz) | Amplitude (Hz) | DF | t | p |
|---|---|---|---|---|---|
| Beta | 13-30 | 50-200 | 10 | 0.23 | 0.822 |
| Low-Phase | 1-20 | 20-200 | 10 | 0.03 | 0.973 |
| High-Amp | 1-30 | 75-200 | 10 | −2.44 | *0.035 |
| Low-Phase/Low-Amp | 1-20 | 20-50 | 10 | −0.61 | 0.554 |
| Low-Phase/High-Amp | 1-20 | 50-200 | 10 | 0.55 | 0.594 |
| High-Phase/Low-Amp | 20-30 | 30-50 | 10 | 1.00 | 0.342 |
| High-Phase/High-Amp | 20-30 | 50-200 | 10 | 0.65 | 0.528 |

Example 3

Figures 13A, 13B, 13C, 13D, 13E, 13F:
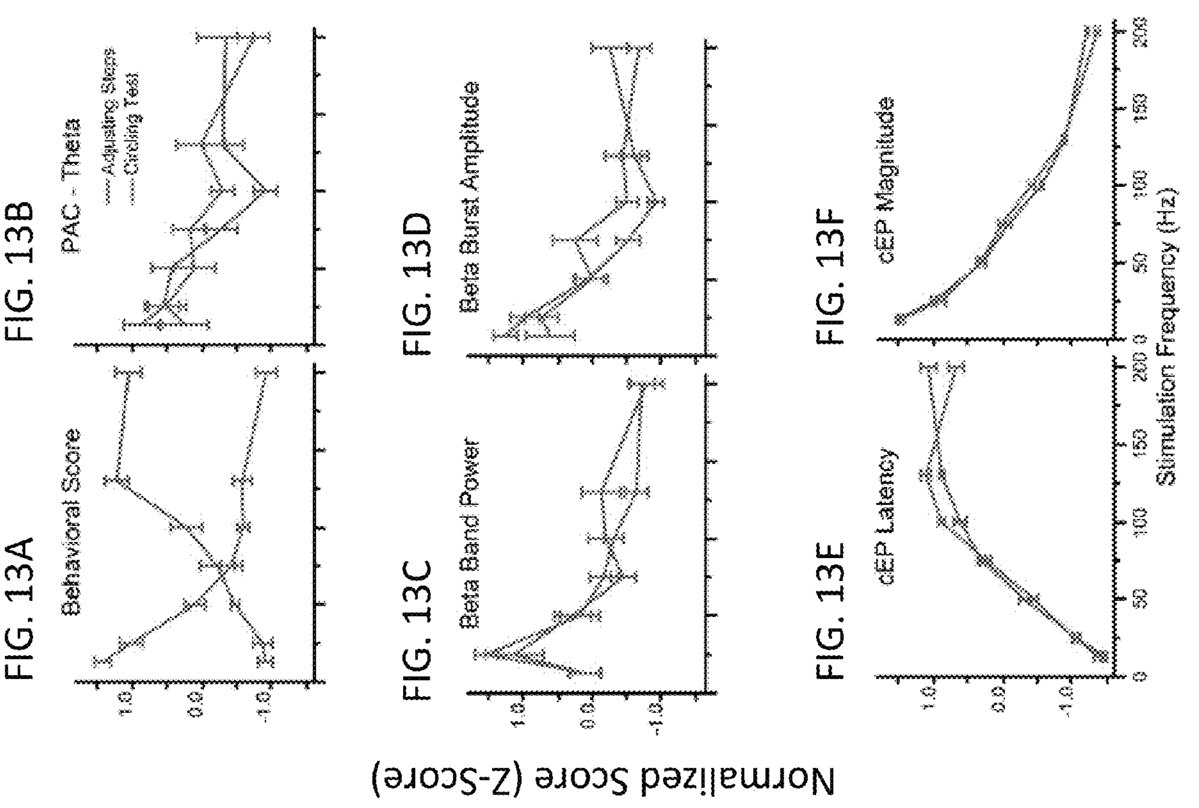
FIGS. 13A-13F: Behavioral scores and selected biomarker values across a range of stimulation frequencies during two behavioral tasks. In each panel, the score for the adjusting steps task is in blue (n=8) and the methamphetamine-induced circling task is in red (n=10). Plotted are the average normalized (Z-Score) values across animals, with error bars indicating the SEM.

Correlation Between Electrophysiological Biomarkers and Symptom Reduction. In the second set of experiments, the per-animal correlations were determined between two quantitative behavioral measurements of symptom and five different cortical biomarkers: the cEP magnitude, cEP latency, spectral power, spectral bursting, and PAC (FIG. 13). Multiple metrics were quantified for each of the spectral features, (e.g., low-beta and high-beta power), but only the metric that had the highest average correlation with behavior was used for subsequent analysis. For the spectral power, the feature with the strongest correlation with behavior was the beta band power (13-30 Hz), for spectral bursting it was the average amplitude of the low-beta (13-20 Hz) bursts, and for PAC it was the theta/low-amplitude (phase 1-8 Hz, amplitude 10-50 Hz) range (FIG. 14). Across both behavioral metrics, the two cEP biomarkers, and especially the cEP magnitude, consistently exhibited the strongest average correlation with symptom reduction, with little variation between animals (FIG. 14). The lower average correlations for the other biomarkers were due to the large variation between animals, as some rats had their strongest correlations with beta band power and PAC, while others exhibited very weak correlations. This is likely because only those rats with high baseline beta band power would exhibit strong correlations, similar to the observation that elevated beta band power is not always seen in PD patients.

Figures 15A, 15B, 15C:
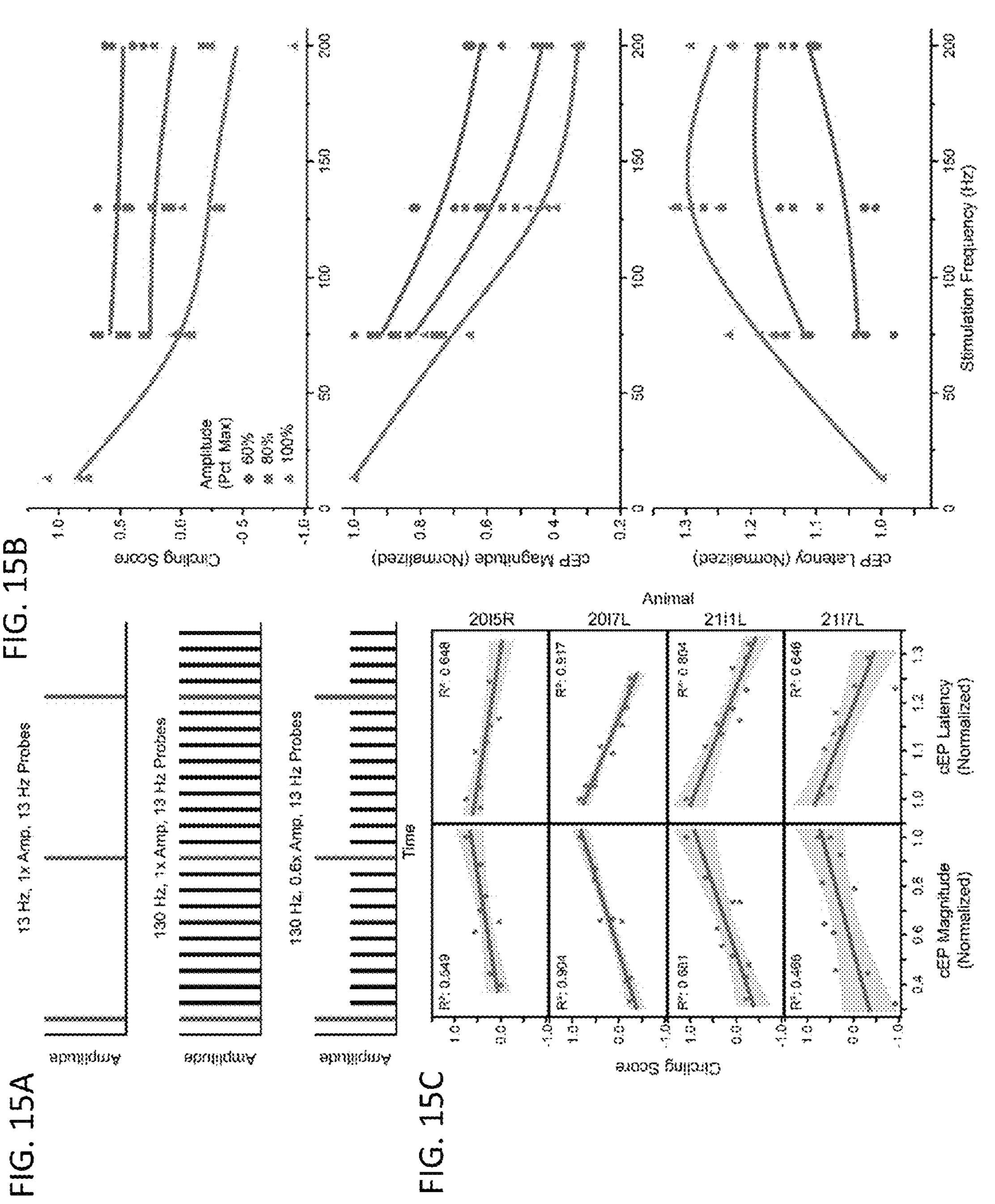
FIGS. 15A-15C: Correlation of cEP magnitude and latency with methamphetamine induced circling across stimulation frequencies and amplitudes.

In a subset of rats (n=4), an additional experiment was performed to confirm further that the correlation between symptom reduction and the cEP biomarkers holds across stimulation amplitude as well as stimulation frequency. A probe-pulse technique was used (see Material and Methods) to maintain consistent cEP measurements across stimulation amplitudes, testing four stimulation frequencies (13, 75, 130, 200 Hz) at three amplitudes (60%, 80%, 100%). All four animals showed strong correlations with symptom reduction for both cEP magnitude and latency (FIG. 15), and these results confirm the robust correlation between cEP features and symptom reduction across stimulation conditions.

What is claimed is:

1. A method of determining efficacy of a neuromodulation therapy based on evoked potential (EP), the method comprising:

(i) administering a first functional stimulation train superimposed with a second probe stimulation train to neural tissue of a subject according to stimulation parameter settings, and obtaining a reference EP recording from the subject; and (ii) altering at least one stimulation parameter of the first functional stimulation train with respect to the reference EP recording, and obtaining a variable EP recording from the subject;

wherein at least one different feature of the variable EP recording obtained by altering the at least one stimulation parameter correlates with a disease indication, a change in symptom, and/or a change in a side effect; and wherein activation during stimulation of the subject's neural tissue for each of the reference EP recording and the variable EP recording is quantified on a per-second basis by summing individual responses to multiple repetitions of pulses within a stimulation train during a specified interval of time.

2. The method of claim 1, wherein the at least one different feature of the variable EP recording obtained by altering the at least one stimulation parameter correlates with charge, energy, and/or power required for stimulation.

3. The method of claim 1, wherein the variable EP recording is obtained from at least a second timepoint with respect to the reference EP recording.

4. The method of claim 1, wherein the at least one stimulation parameter comprises: (i) number and/or location of active electrode contacts; (ii) stimulation amplitude and polarity delivered to each contact; (iii) stimulation pulse repetition frequency; (iv) stimulation pulse duration; (v) stimulation pulse shape; and (vi) temporal pattern of stimulation.

5. The method of claim 4, wherein the temporal pattern of stimulation comprises duty cycle, bursts, random patterns, and non-random patterns.

6. The method of claim 1, wherein the at least one feature of the reference or variable EP recording comprises: (i) maximum peak voltage; (ii) peak latency; (iii) voltage differences from a maximum voltage; (iv) minimum trough value; (v) mean waveform value; (vi) voltage standard deviation; (vii) sum of voltage squared; (viii) voltage difference from the voltage at a set time point; and (ix) signal power present in specific spectral bands of the EP and any combinations thereof.

7. The method of claim 1, wherein the reference EP recording and the variable EP recording are obtained by averaging individual responses to multiple repetitions of pulses within a stimulation train.

8. The method of claim 1, wherein the reference EP recording and the variable EP recording are obtained as part of a closed-loop stimulation protocol.

9. The method of claim 1, wherein the method further comprises repeating steps (i) and (ii) to generate a variable EP signature that comprises a plurality of different features with respect to the reference EP.

10. The method of claim 9, wherein the variable EP signature: (i) correlates with a disease indication, a change in symptom, and/or a change in side effect; and/or (ii) correlates with charge, energy, and/or power required for stimulation.

11. The method of claim 1, wherein the method further comprises altering the at least one stimulation parameter to treat a symptom and/or reduce a side effect in the subject.

12. The method of claim 11, wherein the treatment is provided to the subject as part of deep brain stimulation (DBS), spinal cord stimulation (SCS), sacral nerve stimulation (SNS), vagus nerve stimulation (VNS), peripheral nerve stimulation (PNS), or cranial nerve stimulation.

13. A method of determining efficacy of a neuromodulation therapy based on evoked potential (EP), the method comprising:

(i) administering a first functional stimulation train superimposed with a second probe stimulation train to neural tissue of a subject according to stimulation parameter settings, and obtaining a reference EP recording from the subject; and (ii) obtaining a variable EP recording from the subject using stimulation parameters for the second probe stimulation train that are identical with respect to the reference EP recording;

wherein at least one different feature of the variable EP recording correlates with a disease indication, a change in symptom, and/or a change in a side effect; and wherein activation during stimulation of the subject's neural tissue for each of the reference EP recording and the variable EP recording is quantified on a per-second basis by summing individual responses to multiple repetitions of pulses within a stimulation train during a specified interval of time.

14. The method of claim 13, wherein the disease indication, the change in symptom, and/or the change in a side effect comprises alterations in network state, ion accumulation, movement of the electrode, synaptic plasticity, neural excitability, changes in the surrounding tissue impedance, disease progression, the medication status of the patient, changes in the state of the patient, changes in the response to stimulation, and any combinations thereof.

15. The method of claim 13, wherein the at least one different feature of the variable EP recording correlates with charge, energy, and/or power required for stimulation.

16. The method of claim 13, wherein the at least one stimulation parameter comprises: (i) number and/or location of active electrode contacts; (ii) stimulation amplitude and polarity delivered to each contact; (iii) stimulation pulse repetition frequency; (iv) stimulation pulse duration; (v) stimulation pulse shape; and (vi) temporal pattern of stimulation.

17. The method of claim 13, wherein the at least one feature of the reference or variable EP recording comprises: (i) maximum peak voltage; (ii) peak latency; (iii) voltage differences from a maximum voltage; (iv) minimum trough value; (v) mean waveform value; (vi) voltage standard deviation; (vii) sum of voltage squared; (viii) voltage difference from the voltage at a set time point; and (ix) signal power present in specific spectral bands of the EP and any combinations thereof.

18. The method of claim 13, wherein the variable EP recording is obtained from at least a second timepoint with respect to the reference EP recording.

19. The method of claim 13, wherein the reference EP recording and the variable EP recording are obtained by averaging individual responses to multiple repetitions of pulses within a stimulation train.

20. The method of claim 13, wherein the reference EP recording and the variable EP recording are obtained as part of a closed-loop stimulation protocol.

21. The method of claim 13, wherein the method further comprises repeating steps (i) and (ii) to generate a variable EP signature that comprises a plurality of different features with respect to the reference EP.

22. The method of claim 13, wherein the method further comprises altering the at least one stimulation parameter to treat a symptom and/or reduce a side effect in the subject.

23. A method of determining efficacy of a neuromodulation therapy based on evoked potential (EP), the method comprising:

(i) administering a first functional stimulation train superimposed with a second probe stimulation train to neural tissue of a subject according to stimulation parameter settings to obtain a reference EP recording; and (ii) altering at least one stimulation parameter of the first functional stimulation train with respect to the reference EP recording to obtain a first variable EP recording; and obtaining a second variable EP recording using stimulation parameters for the second probe stimulation train that are identical with respect to the reference EP recording;

wherein at least one different feature of the first and/or second variable EP recording correlates with a disease indication, a change in symptom, and/or a change in a side effect.

* * * * *